(12) United States Patent
Bhola et al.

(10) Patent No.: US 9,098,523 B2
(45) Date of Patent: Aug. 4, 2015

(54) METHOD AND APPARATUS FOR COMPRESSING AND DECOMPRESSING GENETIC INFORMATION OBTAINED BY USING NEXT GENERATION SEQUENCING (NGS)

(71) Applicant: Samsung Electronics Co., Ltd., Gyeonggi-do (KR)

(72) Inventors: Vishal Bhola, New Delhi (IN); Iqbal Nadir Cazi, Pune (IN); Shyamsunder Ajit Bopardikar, Bangalore (IN); Rama Srikanth Mallavarapu, Bangalore (IN); Rangavittal Narayanan, Bangalore (IN); Tae-Jin Ahn, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 94 days.

(21) Appl. No.: 13/715,908

(22) Filed: Dec. 14, 2012

(65) Prior Publication Data
US 2013/0204851 A1 Aug. 8, 2013

(30) Foreign Application Priority Data

Dec. 15, 2011 (IN) .......................... 4405CHE2011PS
Dec. 5, 2012 (IN) .......................... 4405CHE2011CS
Dec. 11, 2012 (KR) .......................... 10-2012-0143620

(51) Int. Cl.
*G06F 17/30* (2006.01)
*G06F 19/28* (2011.01)
*G06F 19/22* (2011.01)

(52) U.S. Cl.
CPC .......... *G06F 17/30153* (2013.01); *G06F 19/28* (2013.01); *G06F 19/22* (2013.01)

(58) Field of Classification Search
CPC ..................... G06F 17/3015; G06F 17/30153
USPC ...................................... 707/693; 702/19, 20
See application file for complete search history.

(56) References Cited

U.S. PATENT DOCUMENTS

| 8,798,936 B2 * | 8/2014 | Bauer et al. ..................... 702/19 |
| 2008/0133519 A1 | 6/2008 | Indeck et al. |

(Continued)

FOREIGN PATENT DOCUMENTS

| JP | 2012-078880 A | 4/2012 |
| KR | 1020040070438 A | 8/2004 |

(Continued)

OTHER PUBLICATIONS

Ansorge, Wihelm J., "Next-generation DNA sequencing techniques," *New Biotechnology*, 25, 4, 195-203 (2009).

(Continued)

*Primary Examiner* — Hares Jami
(74) *Attorney, Agent, or Firm* — Leydig, Voit & Mayer, Ltd.

(57) ABSTRACT

Provided are methods and apparatuses for compressing genetic information, the methods and apparatuses obtaining read information about reads and alignment information about positions of the reads that are aligned to a reference sequence, and generating a compressed file comprising information about an address of a block corresponding to the aligned reads. Also, a method and apparatus for decompressing genetic information obtains a compressed file with respect to the genetic information, determines an address of a block corresponding to input gene search information, from the compressed file, and selectively decompresses genetic information corresponding to the determined address.

16 Claims, 20 Drawing Sheets

(56) References Cited

U.S. PATENT DOCUMENTS

| | | | |
|---|---|---|---|
| 2010/0138165 A1 | 6/2010 | Fan et al. | |
| 2012/0053845 A1 | 3/2012 | Bruestle et al. | |
| 2012/0095693 A1* | 4/2012 | Ganeshalingam et al. | 702/19 |
| 2012/0102054 A1 | 4/2012 | Popescu et al. | |

FOREIGN PATENT DOCUMENTS

| | | |
|---|---|---|
| KR | 1020040071993 A | 8/2004 |
| KR | 1020110129628 A | 12/2011 |
| KR | 1020120056944 A | 6/2012 |

OTHER PUBLICATIONS

Shendure, J et al., "Next-generation DNA sequencing," *Nature. Biotechnology*, 26, 10, 1135-1145 (2008).

Daily K. et al., "Data structures and compression algorithms for high-throughput sequencing technologies," *BMC Bioinformatics*, 11:514 (2010).

Fritz, Hsi-Yang Markus et al, "Efficient storage of high throughput DNA sequencing data using reference-based compression," Downloaded from genome.cship.org on Feb. 25, 2015—Published by Cold Spring Harbor Laboratory Press, (2011).

* cited by examiner

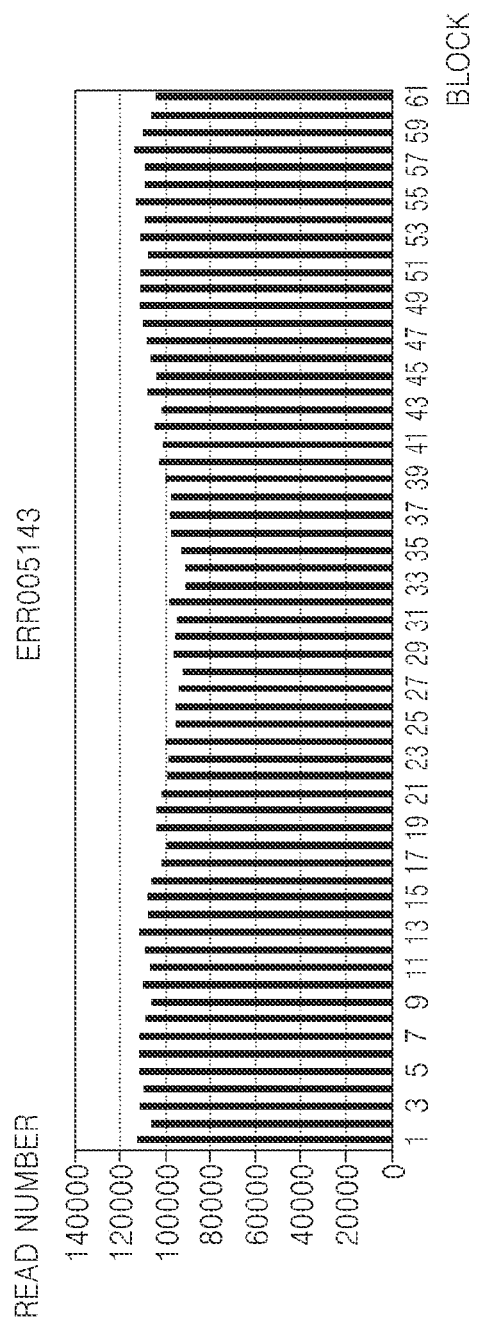

Diff. string : 0ICTCGATC 4SG 3D1 5S TGT 1IA
CIGAR string : 7S 8M 1D 9M 1I 8M

METHOD AND APPARATUS FOR COMPRESSING AND DECOMPRESSING GENETIC INFORMATION OBTAINED BY USING NEXT GENERATION SEQUENCING (NGS)

CROSS-REFERENCE TO RELATED PATENT APPLICATIONS

This application claims priority to Indian Patent Application No. 4405/CHE/2011(PS), filed Dec. 15, 2011, Indian Patent Application No. 4405/CHE/2011(CS), filed Dec. 5, 2012, and Korean Patent Application No. 10-2012-0143620, filed on Dec. 11, 2012. The disclosure of each of these applications is incorporated by reference herein in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,207 Byte ASCII (Text) file named "711878_ST25.txt," created on Mar. 22, 2013.

BACKGROUND

1. Technical Field

The present disclosure relates generally to methods and apparatus for compressing and decompressing genetic information and more particularly to systems and methods for compressing and decompressing sequencing information obtained using a next generation sequencing (NGS) platform or methodology.

2. Description of the Related Art

Parallel sequencing and next generation sequencing (NGS) platforms are rapidly transforming data collection and analysis in genome, epigenome, and transcriptome research fields. NGS technologies have opened fascinating opportunities in life sciences. New fields and applications in biology and medicine are becoming a reality, beyond genomic sequencing.

One application of NGS technologies is variant analysis by aligning the sequencing reads to a reference genome. Due to the high coverage provided by the NGS technologies, the mutations such as SNPs (single-nucleotide polymorphisms), CNVs (copy-number variations) and so on can be detected with high accuracy. These variations can then be analyzed and studied for possible association with pathological conditions like cancer, diabetes, and so on. This has brought the scenario of personalized healthcare and medicine even closer. In a personalized medicine scenario, an immediate access to genomic data in specific areas, for example, genes, axons, and the like, assumes great importance to allow for fast and accurate processing of data so as to detect the mutations or variations of interest.

The number of sequencing reads in NGS files can range from hundreds of millions to billions, depending on the species sequenced and the coverage leading to file sizes of order of MBs (megabytes) to GBs (gigabytes). NGS technology generates huge amounts of genomic data along with multiple annotations, for example, quality scores and other meta-information such as read identifiers, instrument names, flow cell lanes, and so on. The constantly increasing throughput poses challenges on the storage, analysis, and management of the sequencing data. NGS data formats available at present need indexing to allow such an access, adding to the existing problem of managing huge data sizes.

There are several compression methods for NGS data. However, most of the compression methods do not provide access to specific sequencing reads corresponding to a position in the genome. As a result, the file needs to be completely decompressed in order to perform an analysis, even if the target is a small region corresponding to the reference genome.

In view of the above discussion, it is desirable to provide a mechanism that compresses and stores the NGS reads aligned to a reference sequence and provides random access to the reads relative to the reference genome. Furthermore, it is desirable to provide a mechanism through which the reads are selectively decompressed without decompressing the entire file.

SUMMARY

The present disclosure provides methods and apparatus for compressing and decompressing genetic information. The genetic information is typically obtained using a next generation sequencing (NGS) platform or methodology and typically includes information such as sequencing reads, quality values/information, annotations, and the like.

The present disclosure also provides a computer-readable recording medium having recorded thereon a program for executing a method in accordance with the present disclosure, by using a computer having one or more processors.

According to an aspect of the present disclosure, there is provided a method of compressing genetic information. The information may be obtained using a next generation sequencing (NGS) platform. The method typically includes obtaining read information about sequencing reads, and alignment information about positions of the reads that are aligned to a reference sequence ("aligned reads"); grouping the aligned reads into one or more blocks corresponding to intervals based on an addressing scheme that divides the reference sequence into the intervals; and generating a compressed file including the addressing scheme and information about an address of the grouped blocks on the reference sequence.

According to another aspect of the disclosure, a method of compressing genetic information is provided. The method typically includes receiving read information including a plurality of sequencing reads and alignment information about positions of reads that are aligned to a reference sequence ("aligned reads"). The read information may be generated by a next generation sequencing (NGS) platform or other sequencing platform. The method also typically includes using an addressing scheme to divide the reference sequence into a plurality of intervals and grouping the aligned reads into one or more blocks corresponding to the intervals. The method further typically includes generating a compressed file that includes an identification of the addressing scheme and information about an address of the grouped blocks on the reference sequence.

According to another aspect of the present disclosure, there is provided a method of decompressing genetic information. The method typically includes operations of receiving a compressed file including encoded genetic information and a reference sequence; receiving gene search information (e.g., input by a user); obtaining address information of blocks that are grouped on the reference sequence based on an addressing scheme, from the compressed file; determining an address of a block corresponding to the gene search information using the obtained address information; and selectively decompressing annotation information corresponding to the determined address using the obtained reference sequence and the compressed file.

According to another aspect of the present disclosure, there is provided an apparatus for compressing genetic information The apparatus typically includes a data obtaining unit that receives read information about and alignment information about positions of the reads that are aligned to a reference sequence. The information may be based upon output from a next generation sequencing (NGS) platform or methodology. The apparatus also typically includes a read analyzing unit that groups the aligned reads into one or more blocks corresponding to intervals based on an addressing scheme that divides the reference sequence into the intervals; and a compressing unit that generates a compressed file including the addressing scheme and information about an address of the grouped blocks on the reference sequence.

According to another aspect of the present disclosure, there is provided an apparatus for decompressing genetic information. The apparatus typically includes a data obtaining unit that receives a compressed file including encoded genetic information and a reference sequence; an addressing unit that obtains or determines address information of blocks that are grouped on the reference sequence based on an addressing scheme, from the compressed file; a read analyzing unit that determines an address of a block corresponding to gene search information (which may be input, e.g., by a user) using the obtained address information; and a decompressing unit that selectively decompresses annotation information corresponding to the determined address using the obtained reference sequence and the compressed file.

According to another aspect of the present disclosure, there is provided a non-transitory computer-readable recording medium having recorded thereon a program for executing a method of compressing genetic information or a method of decompressing genetic information as provided in the present disclosure. Execution of the program by a processor or multiple processors causes the processor(s) to implement the compression or decompression methodology. The computer readable medium may include a memory unit, or a storage unit of a computing apparatus (e.g., RAM or ROM), or a portable medium or drive such as a DVD, CD, thumb drive, hard drive, etc, that is readable by a computing apparatus.

BRIEF DESCRIPTION OF THE DRAWINGS

The above and other features and advantages of the present disclosure will become more apparent by describing in detail exemplary embodiments thereof with reference to the attached drawings in which:

FIGS. 11(a) through 11(c) illustrate distributions of reads with respect to reference positions for three different files, according to embodiments of the present disclosure;

DETAILED DESCRIPTION

Figure 1:
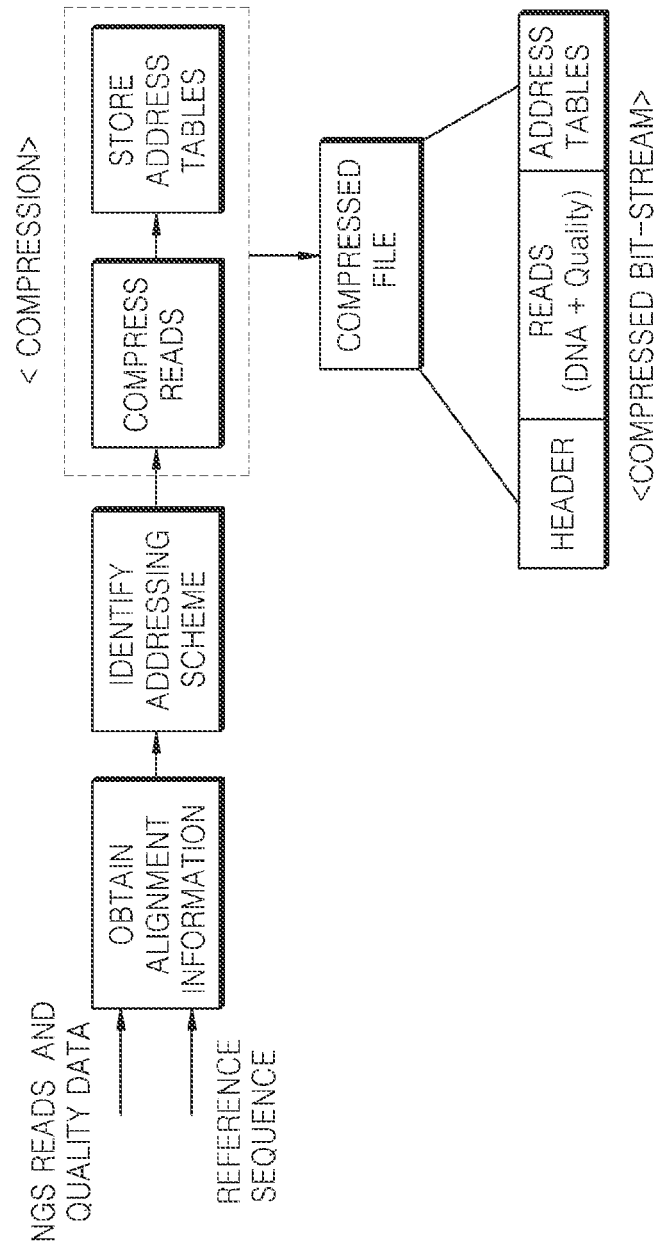
FIG. 1 is a block diagram illustrating compression of sequencing reads and quality information with providing a random access, according to an embodiment of the present disclosure.

Hereinafter, the present disclosure will be described in detail by explaining exemplary embodiments of the invention with reference to the attached drawings.

The embodiments herein achieve methods and systems for efficiently compressing genomic data, providing a random access and selective decoding with respect to the sequencing reads ("reads") corresponding to a specific region on a reference genome or a reference sequence. Further, the embodiments herein provide a format for storing not only a compressed read and quality information, but also storing annotations and providing a random access to the annotations. Here, the annotations may be selectively decoded without decompression of the reads and the genomic data.

The genomic data from NGS technologies is obtained in the form of billions of reads with DNA sequence data, quality scores, and other sequencing specific information. The genomic data is typically stored in a FASTQ file format. Furthermore, the DNA reads may be aligned in a relevant or suitable reference sequence by using alignment tools like BWA, bowtie, SSAHA2, and the like. The output of the alignment tools is generally stored as a structural alignment map (SAM) or a binarized version of an SAM file called a BAM file. Also, in some embodiments, not only may SAM/BAM files be used, but also any file that provides alignment information for each read may be used. The methods and systems according to the present embodiments encode the reads and quality information using the alignment information so as to achieve efficient compression.

Furthermore, the methods and systems according to the embodiments may be used to encode other components of standard file formats such as SAM/BAM.

In certain aspects, the compression for the reads and quality information is implemented in a 2-pass fashion, and statistics are collected from the partial or full first pass. The statistics may be used to identify the most efficient encoding methods for the reads and quality information. The statistics may also be used to identify the best possible addressing schemes, which will define the performance of a random access to selectively decompress the reads relative to a reference position.

In some embodiments, annotations can be single nucleotide polymorphisms (SNPs), methylation information, copy-number variation (CNV), or the like, which can also be stored in the compressed file along with the reads and quality scores.

In some embodiments, the statistics are collected in the first partial pass for various fields, for example, variation information, and quality scores. The statistics are used to identify a desirable (e.g., the best) encoding method for each of the fields by comparing the estimated costs of encoding.

Further, by using the alignment information, the number of reads aligning to reference intervals (i.e., the starting position should lie within the reference interval) is obtained. Here, there may be various methods of distributing the reads into the input files. In some embodiments, three possible cases of read distribution are provided.

In case 1 of read distribution, the reads are distributed uniformly throughout the length of the reference sequence. In case 2, the reads are uniformly distributed only in some specific intervals on the reference sequence and are non-uniformly distributed elsewhere. In the case 3, it is considered that the reads are non-uniformly distributed within reference intervals.

Further, two different addressing schemes for storing the reads in a block wise manner are described below. Other addressing schemes as may be apparent to one skilled in the art may be used. The first addressing scheme is known as constant interval on reference (CIR).

In the CIR addressing scheme, each block includes reads that exist in an interval having a starting position with a constant length on the reference sequence. In the CIR addressing scheme, the number of blocks $N_{Blocks}$ may be represented as the greatest integer that is close to the ratio of the reference sequence length to the interval length. This is obtained by using Equation 1.

$$N_{Blocks}=[\text{Reference sequence length/Interval length}] \quad \text{[Equation 1]}$$

Referring to Equation 1, $N_{Blocks}$ indicates the number of blocks, and brackets in Equation 1 (i.e., "[" and "]") indicate a calculation to round off the value inside the brackets to the greatest integer that is close to the value of the ratio inside the brackets.

When a large percentage of the blocks are empty, e.g., when a large percentage of blocks having no reads within them exist, starting memory addresses for the empty blocks are not stored. Instead, a bit-masking is employed, which signifies the presence or absence of reads for each of the blocks. Hence, space on the memory locations for these empty blocks is saved by utilizing just one bit per block. Thus, there exist two variations of CIR, which includes CIR without bit-masking and CIR with bit-masking.

In an embodiment of CIR without bit-masking, the starting memory locations for the non-empty as well as empty blocks are stored. The addressing scheme (i.e., CIR without bit-masking) may be applied to a case in which there is a set of reads that are similarly distributed.

In an embodiment of CIR with bit-masking, the starting memory locations are stored for only non-empty blocks. The addressing scheme (i.e., CIR with bit-masking) may be applied to a case in which there is a set of reads that are distributed only in some specific intervals on the reference sequence and are non-uniformly distributed elsewhere.

As another addressing scheme, there is a constant number of reads per block (CRB) scheme in which each block holds a constant number of reads. Here, the total number of blocks $N_{Blocks}$ may be represented as the greatest integer that is close to the ratio of number of reads in the input file to the number of reads per block. The (CRB) addressing scheme may be applied to a case in which there is a set of reads that are non-uniformly distributed within the reference intervals. This is obtained by using Equation 2.

$$N_{Blocks}=[\text{Number of reads in the input file/Number of reads per block}] \quad \text{[Equation 2]}$$

Referring to Equation 2, $N_{Blocks}$ indicates the number of blocks, and brackets in Equation 2 (i.e., "[" and "]") indicate a calculation to round off the value inside the brackets to the greatest integer that is close to the value of the ratio inside the brackets.

Different addressing schemes to ensure that the decoding time is reduced are described below.

While a set of reads are decoded from the compressed file in each specified interval on the reference sequence, the speed of decoding depends on the position of the reads within the blocks. In the CIR scheme, as illustrated in FIG. 11(c), when the blocks include the reads that vary, some blocks may include a small number of reads while some other blocks may include a huge number of reads. Thus, there may be a situation in which a number of unnecessary reads are decoded from a particular block before the required set of reads is reached. Thus, it is not possible to estimate the worst-case decoding time with respect to the particular block.

However, in the CRB scheme, regardless of the read distribution, all blocks include an equal number of reads Thus, the worst-case decoding time can be estimated based on the number of reads per block. Thus, the decoding time may be easily estimated based on the number of reads per block. Therefore, the addressing schemes apart from the CIR scheme may increase the decoding speed.

Further, a method of identifying an optimal addressing scheme is described below. For a given set of NGS information samples, the identification of the addressing scheme to be used is done by analyzing the distribution of the reads on the reference genome.

First, the reference genome is divided into constant size intervals of suitable length. The reads are then assigned to each block based on the starting position of the reads in reference. Here, only the blocks with a non-zero number of reads are considered for identification of addressing schemes. A variation coefficient $C_v$ is obtained by using Equation 3.

$$C_v=[\sigma/\mu], \quad \text{[Equation 3]}$$

Referring to Equation 3, '$\mu$' indicates an average in the number of reads per block and '$\sigma$' indicates the standard deviation of the number of reads per block. In general, the variation coefficient $C_v$ is used to determine a relative deviation or distribution, so that, as the variation coefficient $C_v$ is decreased, the reads may be distributed near the average.

Thus, $C_v$ provides a form of normalized variance that can be compared against a global threshold to decide whether the given set of reads data is having a uniform distribution or not.

When an identified addressing scheme is a CIR scheme, either a CIR scheme with bit-masking or a CIR scheme without bit-masking may be used.

In certain aspects, it is possible to assume that 'x' indicates the number of blocks which are not zero, and 'y' indicates the number of empty blocks that do not have reads. Also, it is possible to assume that the number of bits used per memory address is N.

In this case, the number of bits required to store addresses in the CIR scheme without bit-masking is obtained by using Equation 4a.

$$N*x+N*y(4 \text{ bytes per memory address}) \quad \text{[Equation 4a]}$$

Also, the number of bits required to store addresses in the CIR scheme with bit-masking is obtained by using Equation 4b.

$$N*x(4 \text{ bytes per memory address})+(x+y)(1 \text{ bit per block for bit-mask}) \quad \text{[Equation 4b]}$$

The CIR scheme with bit-masking may be selected for a case of Equation 4c.

$$[N*x+N*y]>[N*x+(x+y)] \text{ i.e., If } y/(x+y)>1/N \quad \text{[Equation 4c]}$$

Therefore, in a case of (the number of empty blocks/a total number of blocks)>1/N, the CIR scheme with bit-masking may be selected, and otherwise, the CIR scheme without bit-masking may be selected.

For example, the number of bits used per memory address may be calculated as 32 in the above case.

In an embodiment, a user may examine or view the distribution of the reads, which could be provided by the statistics gathering part of the system or any other statistical technique to determine or select the specific addressing scheme. However, according to the present embodiment, the user may determine an addressing scheme according to user preference. If the user selects a certain addressing scheme, the addressing scheme selected by the user may be used, regardless of the determination by the system.

Hereinafter, the embodiments are described with reference to FIGS. 1 through 21. Here, similar reference characters denote corresponding features consistently throughout the figures.

FIG. 1 is a block diagram illustrating compression of reads and quality information with providing a random access, according to an embodiment of the present disclosure.

First, an NGS file, a reference sequence, and alignment information are provided as inputs to the system. The alignment information is used to identify the addressing schemes. In the present embodiment, there exists two addressing schemes; namely, constant interval on reference (CIR) and constant number of reads per block (CRB) for storing the reads in a block wise manner. The method of identifying addressing schemes will be described in detail below.

The DNA (deoxyribonucleic acid) reads aligned to the reference are encoded by using an efficient representation of the difference with the reference sequence. In one embodiment, Arithmetic Coding (AC) is used as the form of entropy encoding to achieve best possible compression. The constant parameters, such as, for example, read length, block length, addressing scheme used, and so on, are stored as part of the header information and are placed at the beginning of the file. The probability tables for the variation information and the quality scores are also stored as part of the header in the compressed file using fixed bytes (i.e., minimum bytes needed to represent these numeric values).

During the encoding process, a buffer is maintained, which holds the starting addresses of the blocks. Once the encoding process is done, these addresses are appended to the file. In the embodiment where the reads are distributed uniformly within some specific intervals and the addressing scheme is selected as CIR, then the bit-mask is also stored in the compressed file. Further, an arithmetic encoder is reinitialized at the beginning of encoding of each block. This is done to keep the encoder and decoder in sync which may otherwise lead to a failure in decompression.

Figure 2:
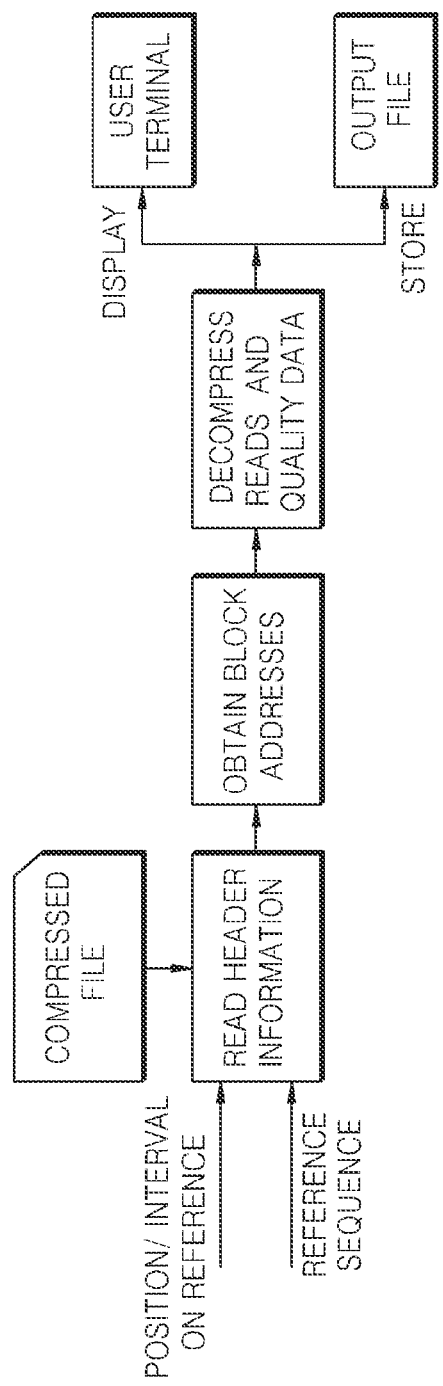
FIG. 2 is a block diagram illustrating decompression of the reads corresponding to a specific interval on a reference sequence, according to an embodiment of the present disclosure.

FIG. 2 is a block diagram illustrating decompression of the reads corresponding to a specific interval on a reference sequence, according to an embodiment of the present disclosure. The inputs for the decompression of the reads includes a compressed file, a reference sequence, and the interval on reference corresponding to which the reads and associated quality scores are decoded. For decompression of reads, the block indices are computed for the input interval by dividing the starting and ending positions of the interval by the length of the constant interval in reference. Then, the bitmask is read, in case the reads are uniformly distributed only in some specific intervals on the reference sequence. In a case where the used addressing scheme is CRB, the blocks corresponding to the start and end of the interval are identified by a binary search operation on the starting positions in reference of each block. This search operation happens on the order of O(log ($N_{Blocks}$)). The block addresses are then obtained and decoding of the reads and quality information is performed. The state of arithmetic encoder is reinitialized at the beginning of the decoding process of each block. Advanced Input/Output (I/O) techniques, such as but not limited to, Memory Mapped files (MMAP) are used to fetch chunks of large files specified by block addresses into memory through on demand paging mechanism, Further, if no interval is specified by the user, complete decompression of the input file is performed. In either of these cases, the decompressed reads and quality information can be displayed to the user or written to a file for further analysis.

In an embodiment, the performance of the random access may depend on the parameters, for example, block size and the addressing scheme used. With the help of block size, the average number of reads to be decoded can be estimated. Larger the block size, the higher the decoding time. Further, the elements that are to be decoded to reach to the block address differ depending on the addressing scheme used.

Figure 3:
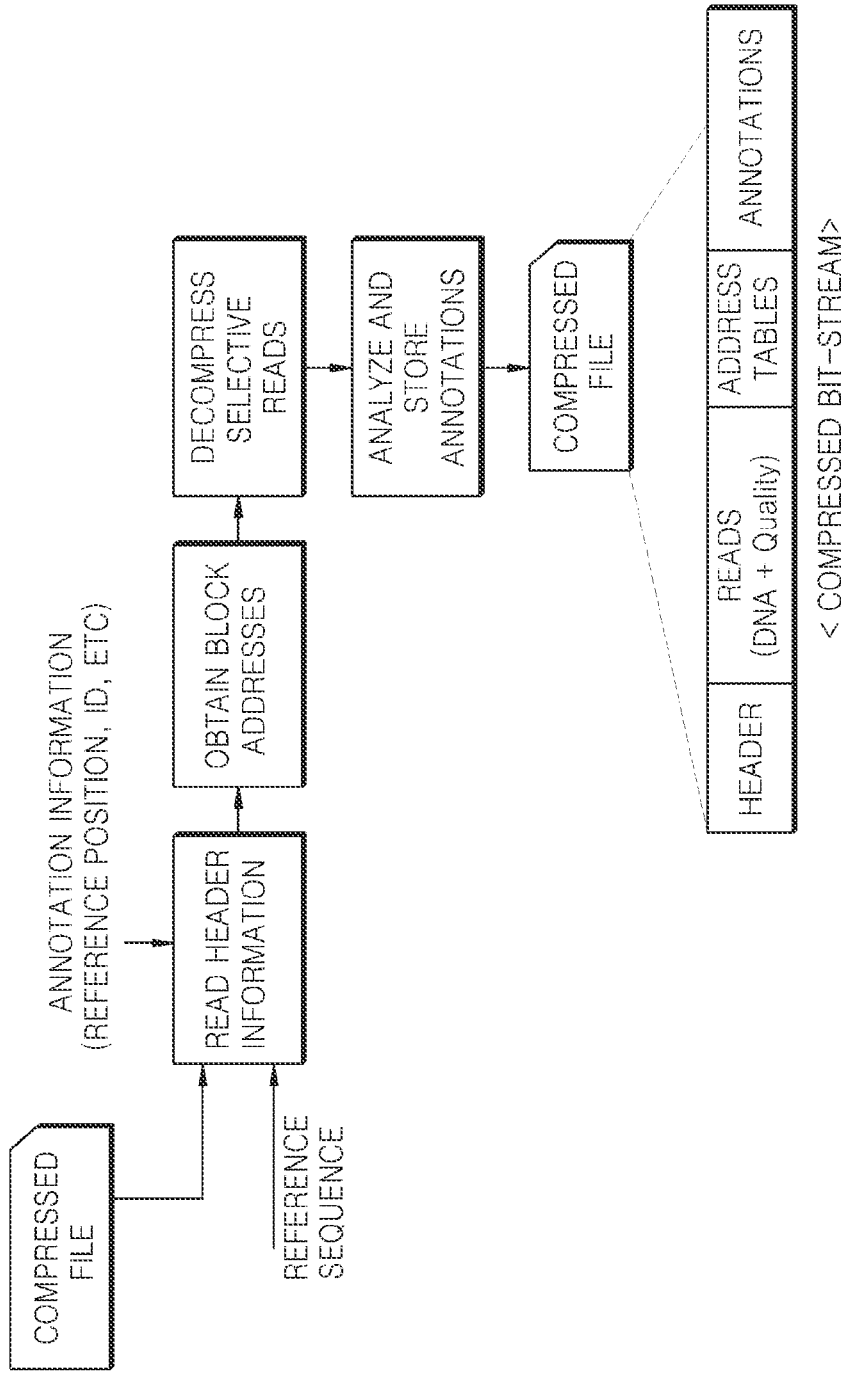
FIG. 3 is a block diagram illustrating storage and compression of annotation information, according to an embodiment of the present disclosure.

FIG. 3 is a block diagram illustrating storage and compression of annotation information, according to an embodiment of the present disclosure. Storage of annotation information to the compressed file includes selective decompression of the input file, if an interval is input to the system. If no interval is provided as an input, then the entire file is decompressed.

Further, the required analysis is then performed on the decompressed reads and the relevant information is stored onto the file. The annotation information present in the input file specifies the location on the reference sequence. Also, the format for annotations should be consistent, so that it can be parsed. The user has to specify, if the added annotations correspond to certain pathology or not. If so, the disease IDs in standard format must be included in the input file with annotation information. If the annotations correspond to pathologies, then they are sorted based on disease ids. For each disease ID, the variations are grouped based on their type, e.g., all SNPs will be stored together, all CNVs will be stored together, and so on. The variations of a single type, e.g., SNPs, are stored in sorted order with respect to the reference position.

In the present embodiment, the annotation information may be downloaded from public or private databases or local repositories and may be output as a file having a format that can be parsed. After the annotations are stored on to the compressed file, the address tables specific to annotations are stored.

Figure 4:
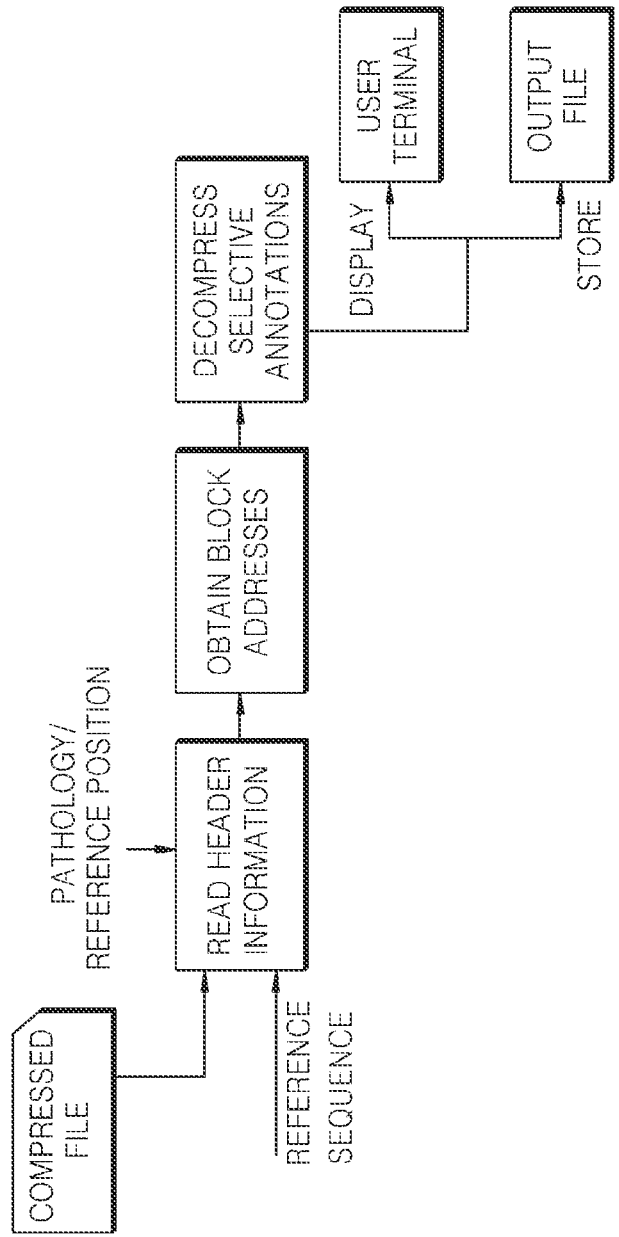
FIG. 4 is a block diagram for description of decompression of the annotation information corresponding to a specific pathology or specific interval on the reference sequence, according to an embodiment of the present disclosure.

FIG. 4 is a block diagram for description of decompression of the annotation information corresponding to a specific pathology or specific interval on the reference sequence, according to an embodiment of the present disclosure. First, an input interval or a pathology condition is provided, e.g. by a user. After the header information is read, the block addresses are read and annotations are compressed from the location or the pathology specified. The reads and quality information corresponding to the interval or pathology may also be viewed by the user or output to a file. In a personalized medicine scenario, a pathology-based ordering of the annotations may be preferred as an input. However, for analysis like SNP calling, methylation information studies and so on, position-based storage of the annotation information may be the preferred choice as an input.

Figure 5:
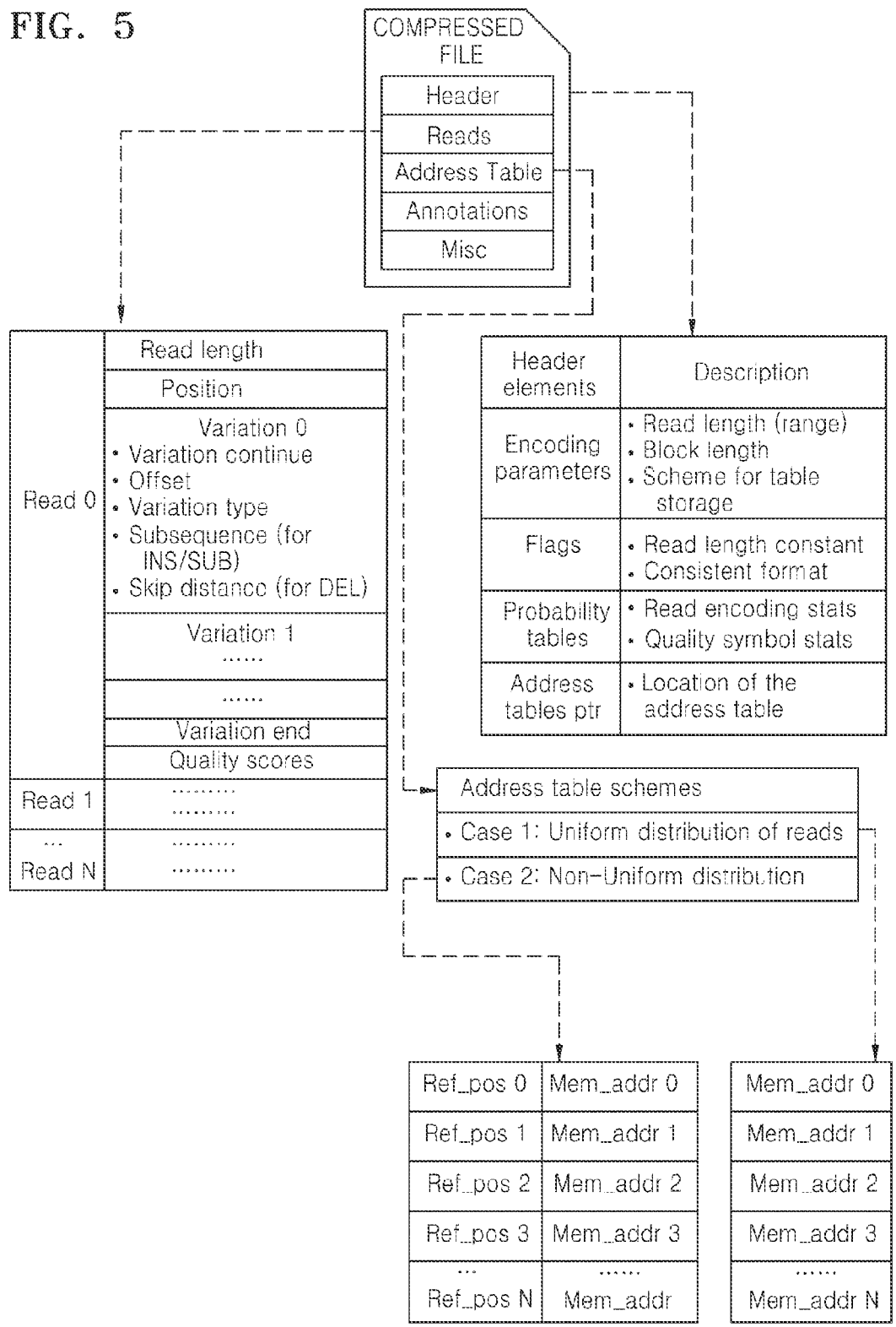
FIG. 5 is an overview illustrating a compressed file format including DNA reads and a quality file, according to an embodiment of the present disclosure.

FIG. 5 is an overview illustrating a compressed file format including DNA reads and a quality file, according to an embodiment of the present disclosure. Referring to FIG. 5, the compressed file format includes a header, reads, annotations, and miscellaneous information. The header includes the header elements; namely, encoding parameters, flags, probability tables, hash tables, and so on. The hash tables provide the information regarding the distribution of reads. The information related to the reads is present within the reads section in the compressed file format. The reads section includes all the reads. Each read will typically have a read length, position, variations, and quality scores.

Figure 6:
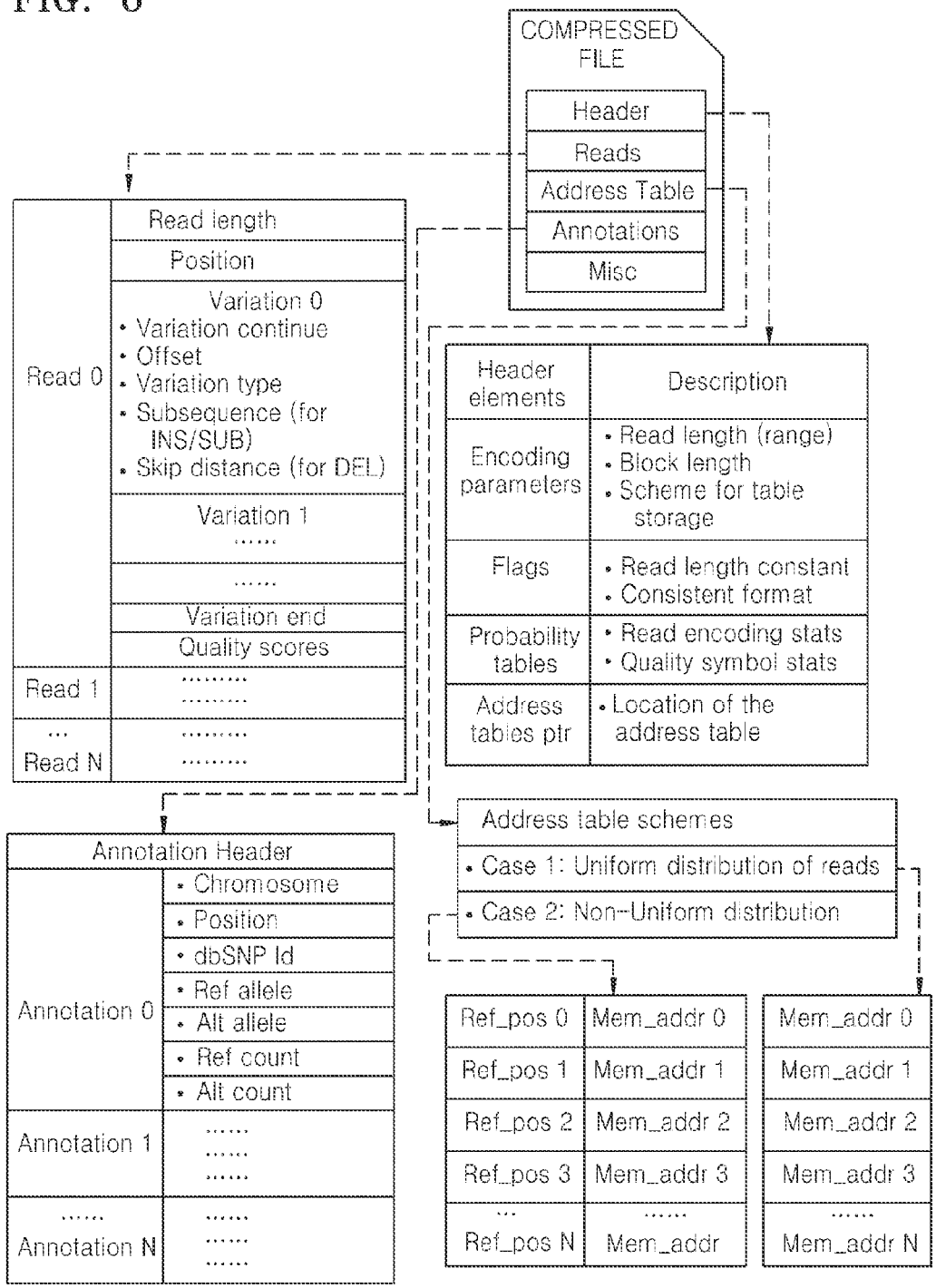
FIG. 6 is an overview illustrating file formats including reads, quality scores, and annotations, according to an embodiment of the present disclosure.

FIG. 6 is an overview illustrating file formats including reads, quality scores, and annotations, according to an embodiment of the present disclosure. Referring to FIG. 6, the compressed file format including reads, quality scores, and annotation information is illustrated. For example, the annotation information includes chromosome, position, reference allele, reference count, and the like.

Figure 7:
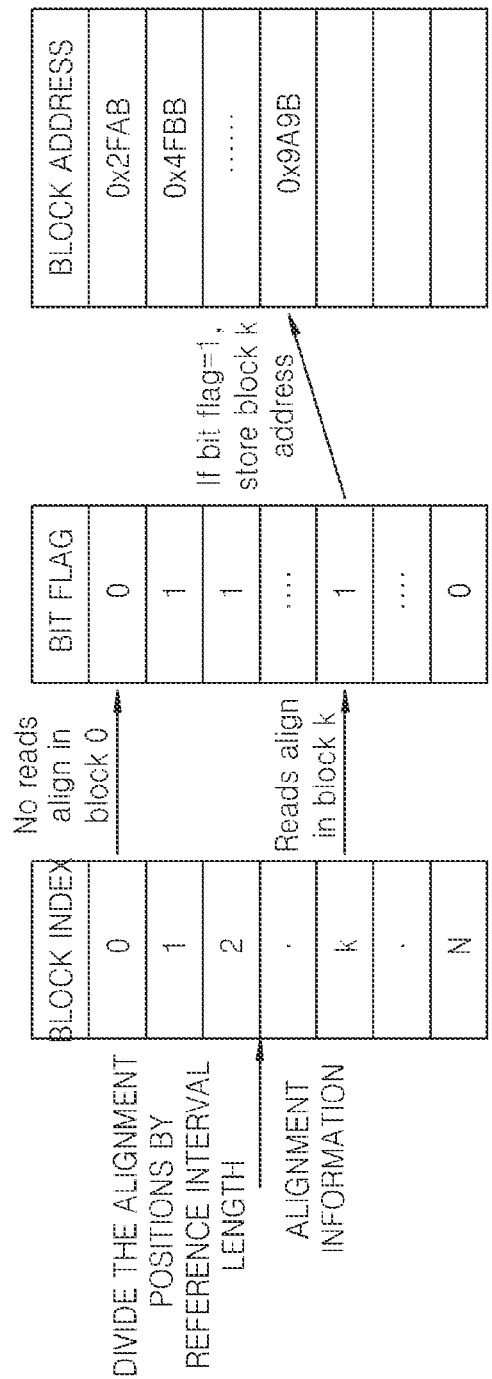
FIG. 7 is a diagram for description of a storage method for the block addresses during compression, according to an embodiment of the present disclosure.

FIG. 7 is a diagram for description of a storage method for the block addresses during compression, according to an embodiment of the present disclosure. With the alignment information, the alignment positions are divided by the length of the reference interval. A block index with the alignment positions is created. If it is found that there are no reads aligning in a specific interval for a particular block, then the bit flag corresponding to the interval is set as zero and the address for this block is not stored onto the compressed file. If there are reads aligning in a block K, for example, then the bit flag corresponding to the interval is set to one and the address for this block is stored onto the compressed file.

Figure 8:
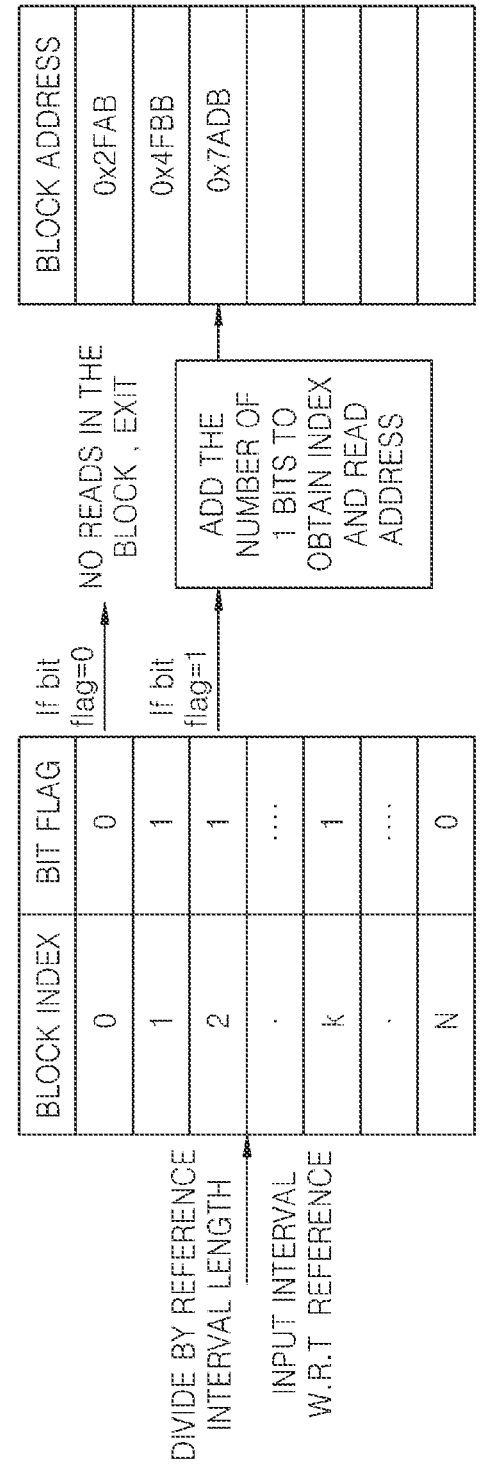
FIG. 8 illustrates a method of retrieving block addresses when a constant interval on reference (CIR) scheme is used as an addressing scheme, according to an embodiment of the present disclosure.

FIG. 8 illustrates a method of retrieving block addresses when a CIR scheme is used as an addressing scheme, according to an embodiment of the present disclosure. The input interval is divided by the interval length to obtain the block index and the corresponding bit flag is read. If the bit flag is read as one, then the block address is read from the file. Further, if the bit flag is read as zero, then the method terminates the operation.

Figure 9:
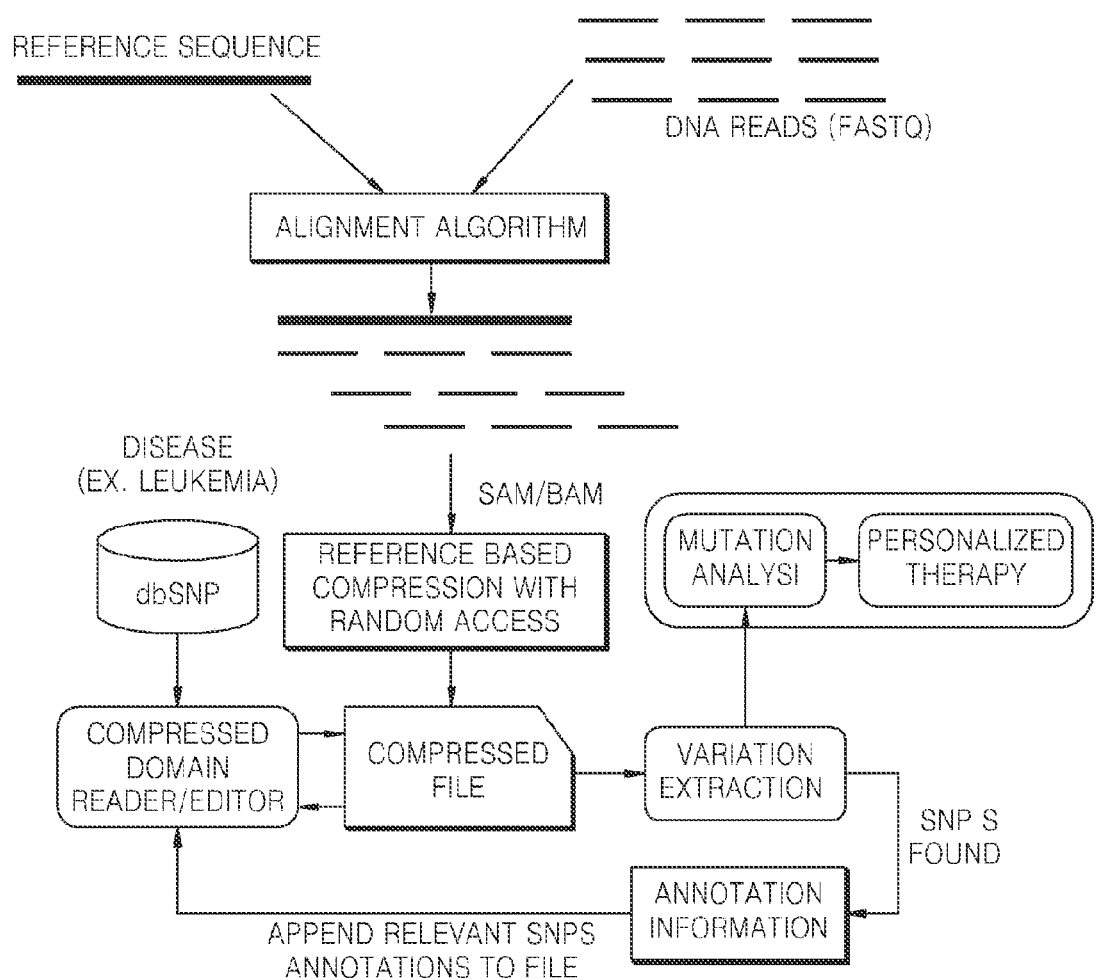
FIG. 9 illustrates a scenario with respect to a method of extracting annotation information and corresponding variations from the compressed file, according to an embodiment of the present disclosure.

FIG. 9 illustrates a scenario with respect to a method of extracting annotation information and corresponding variations from the compressed file, according to an embodiment of the present disclosure. The annotation information may be obtained from a source such as dbSNP (SNP database) or a local repository. The annotation information includes the position(s) on the reference sequence. Then, a selective decompression of the reads aligning to these positions may be done and the relevant information, for example, dbSNP ID (identifier), reference allele, alternate allele, and the like, may be stored into the compressed file with the existing compressed reads and quality information.

Figure 10:
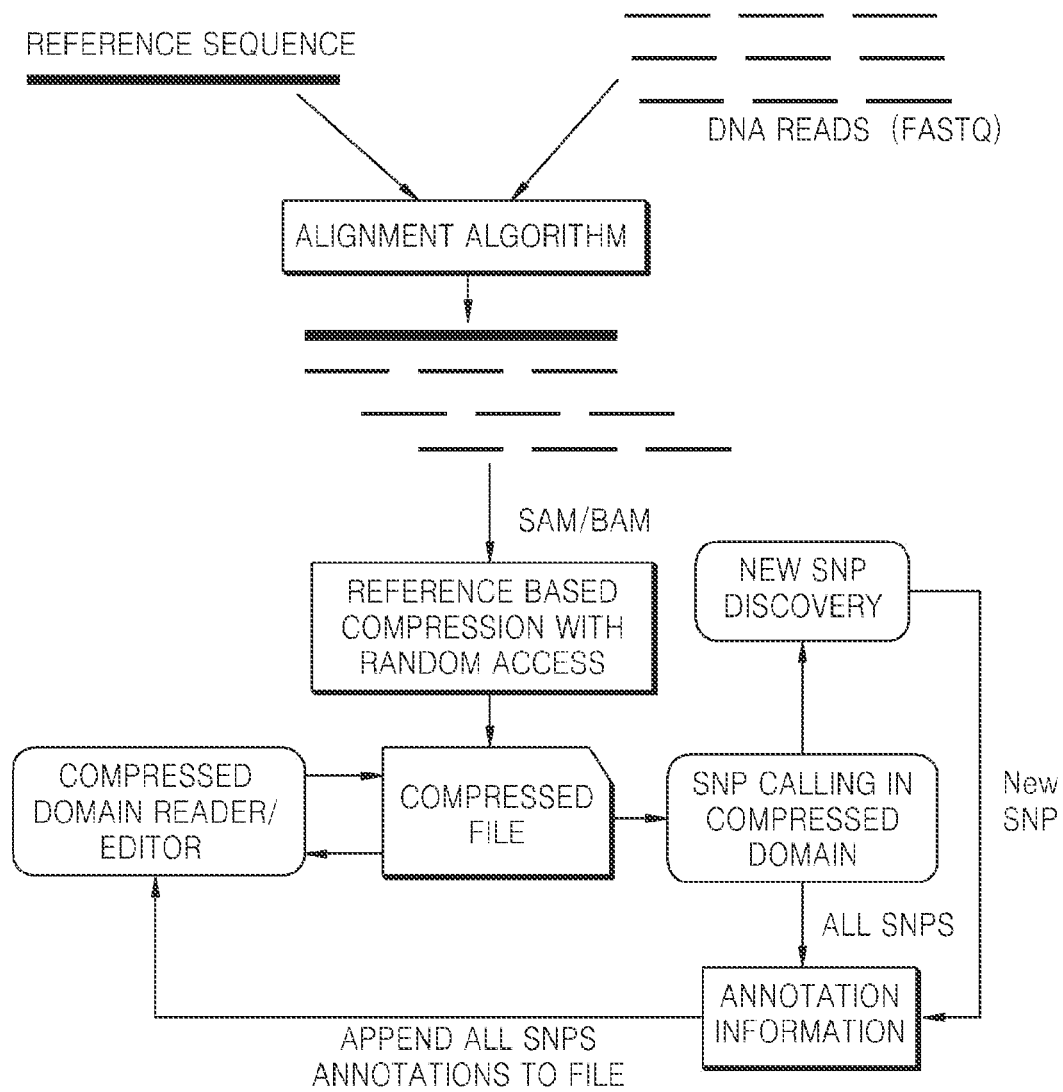
FIG. 10 illustrates a scenario with respect to a method of selectively decompressing the reads and quality information so as to identify the new SNPs, according to an embodiment of the present disclosure.

FIG. 10 illustrates a scenario with respect to a method of selectively decompressing the reads and quality information so as to identify the new SNPs, according to an embodiment of the present disclosure. In this scenario, a selective interval on the reference, which corresponds to a genome, is provides as an input, e.g., by a user. The reads aligning to this interval may be decoded and an analysis such as SNP calling and the like may be done. The results of the analysis may be stored onto the compressed file or may be used in a further analysis so as to find disease association and the like.

Figure 11B:
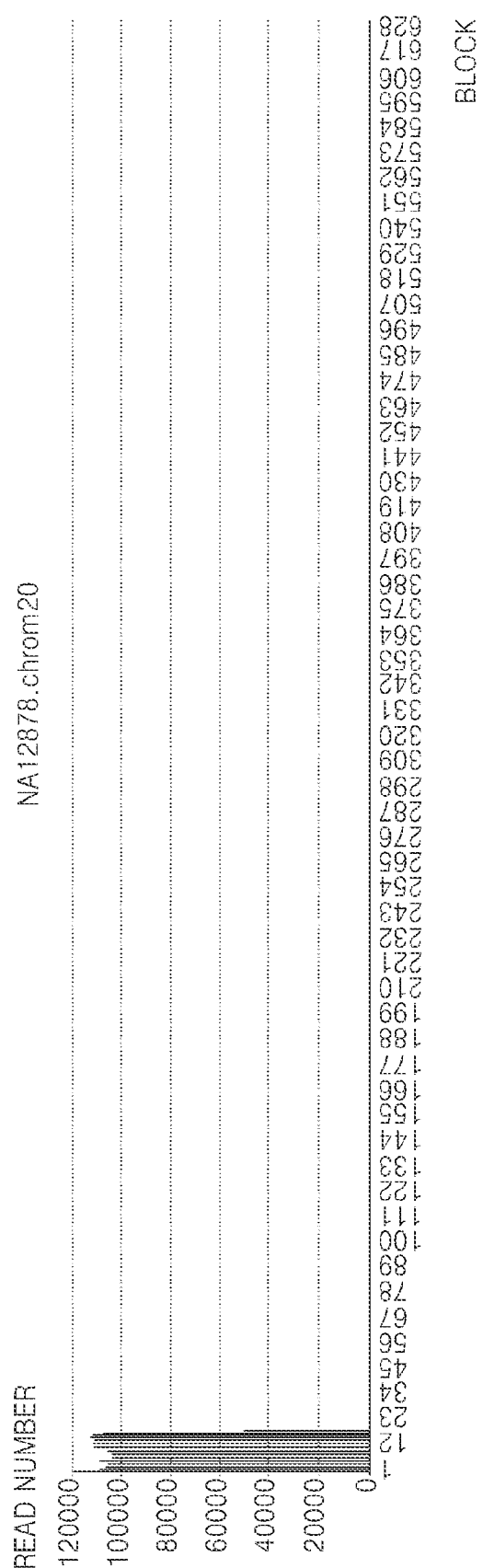
Figure 11C:
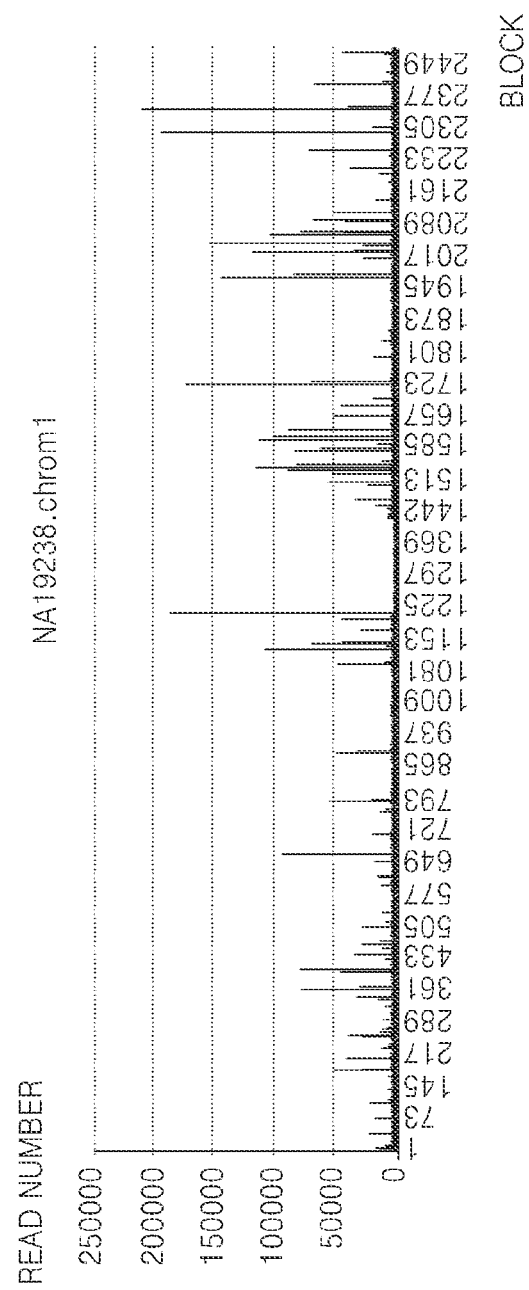

FIGS. 11($a$) through 11($c$) illustrate distributions of reads with respect to reference positions for three different files, according to embodiments of the present disclosure. According to some embodiments, the distribution of reads with respect to the reference position is demonstrated in three cases, as illustrated in FIGS. 11($a$) through 11($c$). Referring to FIG. 11($a$), the reads are distributed uniformly throughout the length of the reference sequence. Referring to FIG. 11($b$), the reads are uniformly distributed and exist only in some specific intervals on the reference sequence. Further, referring to FIG. 11($c$), the reads may not be uniformly distributed within the reference intervals.

Figure 12:
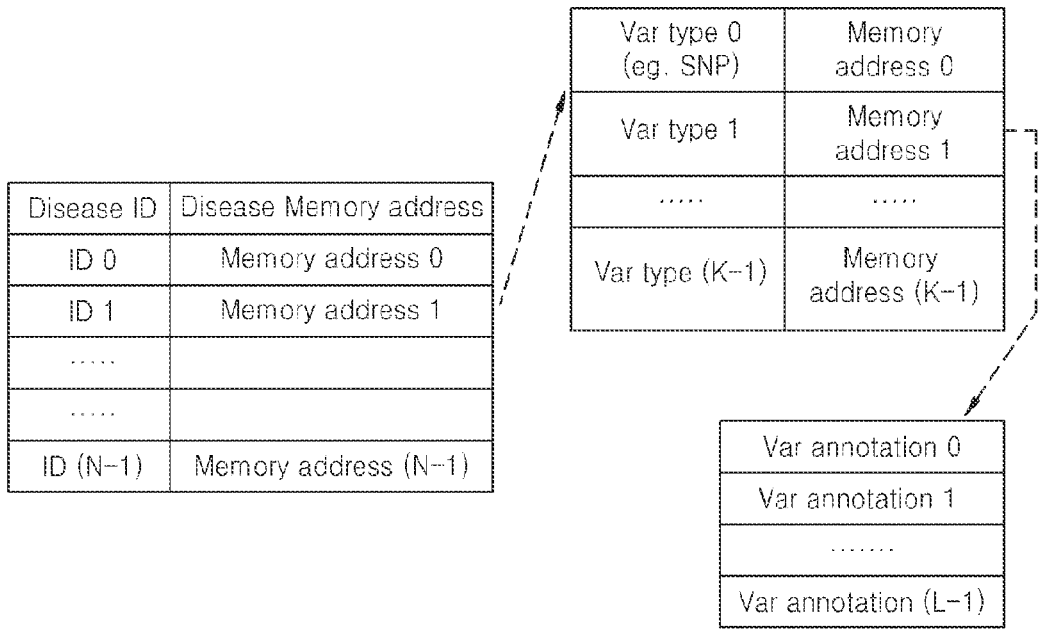
FIG. 12 illustrates the storage format for annotations, according to an embodiment of the present disclosure.

FIG. 12 illustrates a storage format for annotations, according to an embodiment of the present disclosure. The annotation information in this embodiment is stored with the disease ID and the disease memory address, as shown.

Figure 13:
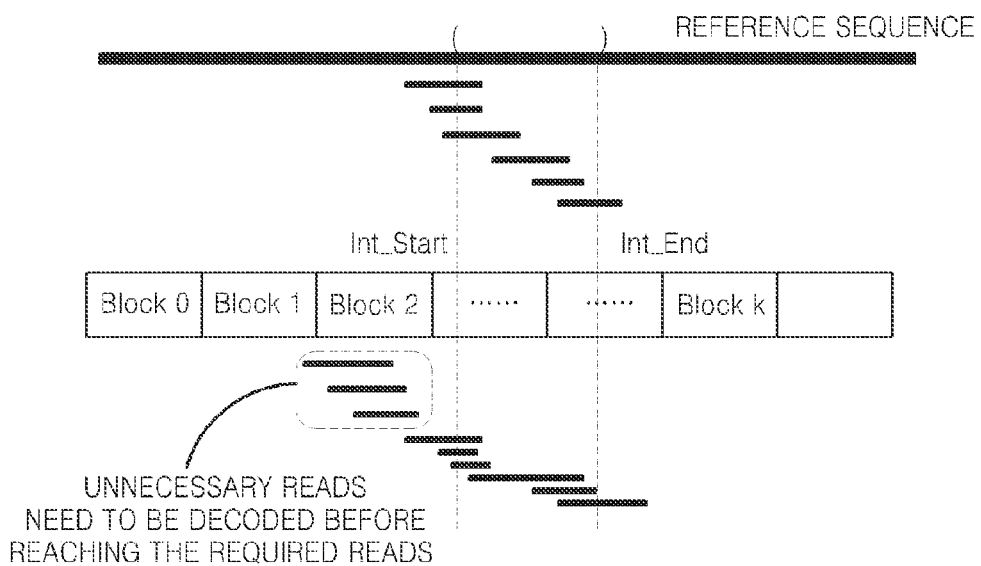
FIG. 13 illustrates the need for different addressing schemes, according to an embodiment of the present disclosure.

FIG. 13 illustrates the need for different addressing schemes, according to an embodiment of the present disclosure. In order to decode the reads that are overlapped with the given interval, the reads are aligned on a reference sequence. Then, the reads are divided to form blocks. Referring to FIG. 13, the blocks that cover the interval represented by int_start and int_end are decoded. The reads in Block 2, which cause a delay in accessing the required reads that exist an interval between int_start and int_end, are decoded before the reads are obtained in the given interval.

In the CIR scheme, as shown in FIG. 11($c$), when the blocks include a varying number of reads, some blocks may include a small number of reads while some blocks may include a large number of reads. Thus, it is difficult to know or determine a decoding time for the specified interval. However, in a case of the CRB scheme, regardless of the read distribution, all blocks include an equal number of reads. Thus, the decoding time may be estimated based on the number of reads per block. Hence, different addressing schemes are required to minimize the accessing time of required reads.

Figure 14:
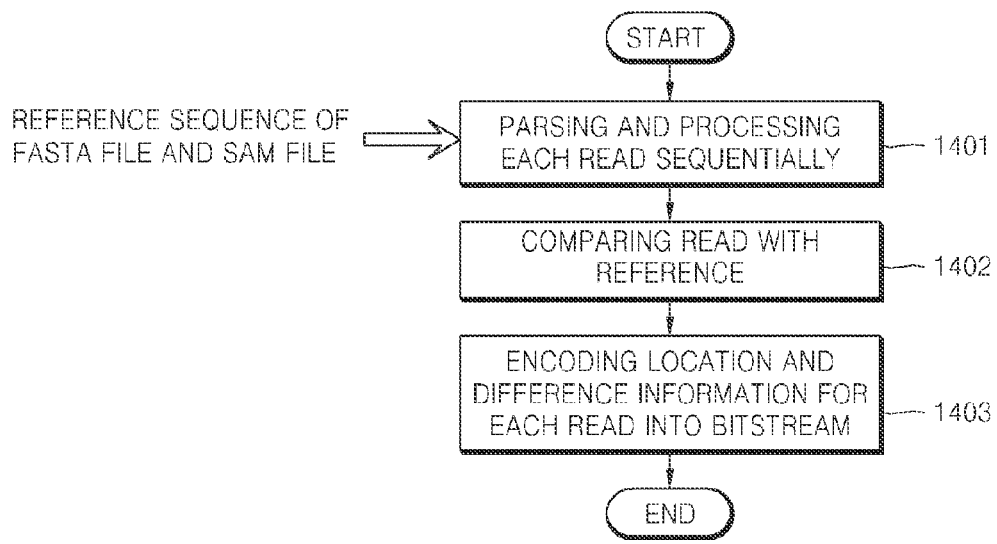
FIG. 14 is a flowchart illustrating a method that involves the compression of reads, according to an embodiment of the present disclosure.

FIG. 14 is a flowchart illustrating a method that involves the compression of reads, according to an embodiment of the present disclosure. A reference sequence of an FASTA file and the SAM file are provided as an input for the compression of reads.

In operation 1401, each of reads is sequentially processed.

In operation 1402, each read is compared with the reference sequence.

In operation 1403, location and difference information for each read are encoded into a bitstream.

In order to compress the aligned reads, each read is sequentially processed. The alignment information related to the read, such as an aligned position in the reference sequence, the CIGAR string, the strand information and the like, is obtained from the SAM file. By comparing the read with the corresponding location in the reference sequence and then processing the alignment information represented by the CIGAR string, variation information for the read is obtained.

For each difference region, an offset of a current difference region is transmitted with an offset of a previous difference region. For a first difference region, a position of a previous difference region is considered as zero.

Then, a type of the variation in the difference region is transmitted. The type of the variation, for example, may include insertion, deletion or substitution. In a case of the deletion, the method encodes a deleted length. If the variation is either the insertion or the substitution, the method encodes the corresponding inserted or substituted nucleotide subsequence.

Further, for softly-clipping, in the present embodiment, an insertion method or a deletion method is used. The softly-clipping as the insertion method is described herein.

A softly-clipped region that occurs at the beginning of the read is considered as an insertion in the beginning of the read. Similarly, a softly-clipped region that occurs at the end of the read is considered as an insertion at the end of the read.

In some embodiments, in the softly-clipping as the substitution method, there are two different approaches.

Figure 15A:
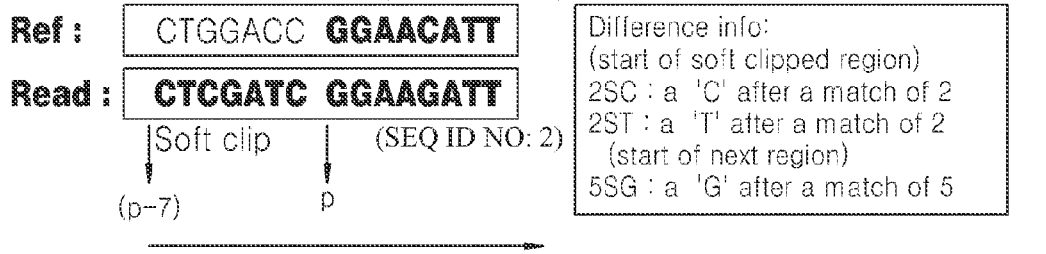
FIG. 15(a) illustrates the first approach of the softly-clipping as the substitution method, according to an embodiment of the present disclosure.

FIG. 15(a) illustrates the first approach of the softly-clipping as the substitution method, according to an embodiment of the present disclosure. In an example of FIG. 15(a), position_in_reference=position_in_reference−7, and a length of a soft clip is 7.

Referring to FIG. 15(a), in the first approach of the softly-clipping as the substitution method, a reference subsequence aligning with the read is extended backwards by an amount equal to the length of the soft clip.

In the present embodiment, the soft clip may be encoded by using the insertion method or the substitution method. During the partial or full first pass in which statistics are collecte, a type of encoding that may be used for the soft-clipping. Also, a user may specify the compression mode.

After the reference subsequence is extended backward, the softly-clipped sequence of nucleotides is treated as a substitution difference and is compared with the reference sequence with respect to matches and mismatches. A new relative position may be a difference between a new reference position and a previous position.

Figure 15B:
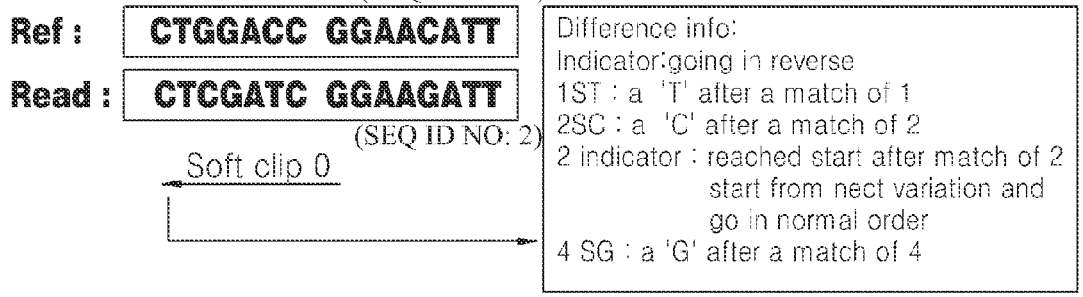
FIG. 15(b) illustrates the second approach of the softly-clipping as the substitution method, according to an embodiment of the present disclosure.

FIG. 15(b) illustrates the second approach of the softly-clipping as the substitution method, according to an embodiment of the present disclosure. Referring to FIG. 15(b), the second approach of the softly-clipping as the substitution method starts from the reference for the read as indicated in the SAM file and proceeds in the reverse direction, coding all the sets of substitutions that occur. When a soft-clip region is coded in a reverse direction, the second approach encodes the remaining difference regions in a normal direction.

Figure 15C:
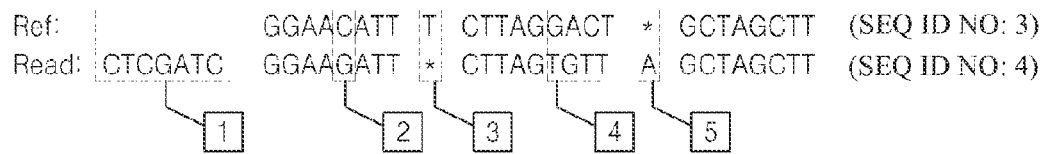
FIG. 15(c) illustrates creation of a difference string and a CIGAR string by comparing the read and the reference sequence, according to an embodiment of the present disclosure.

FIG. 15(c) illustrates creation of a difference string and a CIGAR string by comparing the read and the reference sequence, according to an embodiment of the present disclosure.

With respect to a method of obtaining difference information, the method creates the difference string while the CIGAR string is stored in a SAM file for a certain read.

First, the given read is compared with the reference sequence, and the CIGAR string is processed to represent the variations as illustrated in FIG. 15(c).

Referring to FIG. 15(c), the difference string is obtained by comparing the read with the reference sequence. First, the soft-clip region at the start of the read, "CTCGATC," is treated as an insertion. Hence, the offset of the variation with respect to the previous variation location (0) is transmitted. Also, the type of variation 'I' (insertion) is transmitted along with the inserted bases, i.e., the soft-clipping "CTCGATC."

After a match of length 4, there exists a substitution from 'C' to 'G.' Hence the offset, the type of variation 'S' along with the substituted base is transmitted. Further, after a match of length 3, a deletion of 1 base occurs, i.e., offset=3, type='D,' delete length equals to 1.

Figure 16:
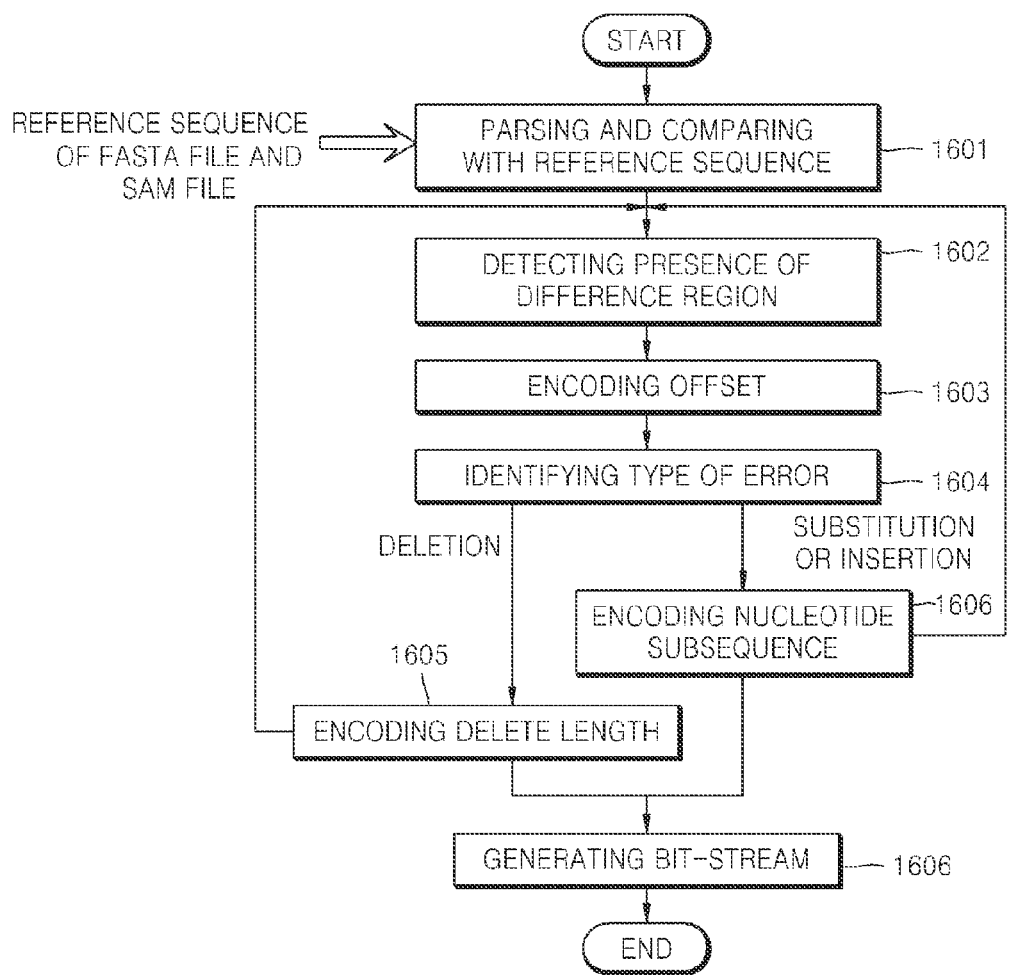
FIG. 16 is a flowchart of a method that involves encoding of the difference information, according to an embodiment of the present disclosure.

Then, after 5 exact matches, a set of 3 consecutive substitutions 'TGT' is found. The consecutive substitutions are represented as 1 substitution. Finally, an insertion of 1 nucleotide, 'A,' is found after an offset of 1 base. In this manner, the difference string is obtained by comparing a given read with the reference sequence, FIG. 16 is a flowchart of a method that involves encoding of the difference information, according to an embodiment of the present disclosure. The reference sequence of a FASTA file and the SAM file are provided as an input for the compression of reads. Referring to FIG. 16, the read is compared with the reference sequence so as to obtain the difference information.

In operation 1601, the read and the reference sequence are parsed and compared.

In operation 1602, the presence of a difference region is detected. When the presence of a difference region is detected, delimiters may be transmitted to indicate the presence of a difference region. Here, entropy coding such as arithmetic encoding is used to transmit a binary indicator. In the present embodiment, one of the available encoding methods is selected. Also, a user may select one of the available encoding methods.

In operation 1603, an offset in the variation is encoded by using entropy coding such as arithmetic encoding.

In operation 1604, the type of error is identified by an entropy coder.

In operation 1605, if the identified error is a deletion error, the deletion length is encoded by using an entropy encoder.

In the present embodiment, the type of error may include a substitution, insertion, or deletion. Also, the insertion or substitution may be used to compress soft-clipping regions or other variation types.

In operation 1606, if the identified error is a substitution error or an insertion error, the nucleotide subsequence is encoded by using an entropy coder.

In a case of the substitution, the nucleotide in the mismatch position in the read is not equal to the nucleotide in the corresponding position in the reference sequence. In the case of the insertion or substitution, the end of the subsequence is represented in a manner that an end of sequence (EOS) symbol is encoded.

Finally, in operation 1607, location and difference information for each read are encoded into a bitstream.

Figure 17:
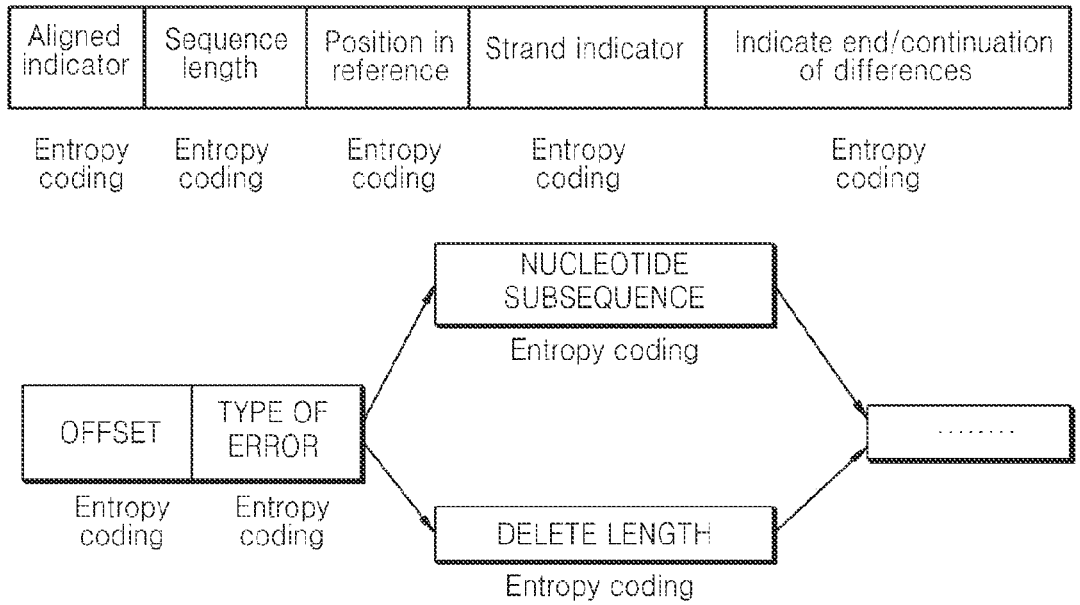
FIG. 17 illustrates a bitstream obtained with respect to aligned reads, according to an embodiment of the present disclosure.

FIG. 17 illustrates a bitstream obtained with respect to aligned reads, according to an embodiment of the present disclosure. Before the variation information for each read is transmitted, the higher level information including the parameters shown in FIG. 17 is transmitted.

The aligned indicator denotes the current read that is encoded as an aligned read. If lengths of the reads throughout the set of sequences are not equal to each other, the read length for the current read using an entropy coder is transmitted by using a sequence length.

The position in which the read aligns in the reference sequence is transmitted by using relative encoding and an integer code such as Fibonacci coding. Alternatively, the difference is considered as a symbol and is encoded by using an entropy coder such as but not limited to an adaptive arithmetic encoder. Whether or not to use integer coding or arithmetic coding is determined based on the statistics observed in the first few hundred thousand reads. The strand information is transmitted to indicate whether the sequence as it occurs in the SAM file has been reverse complemented or not.

Figure 18:
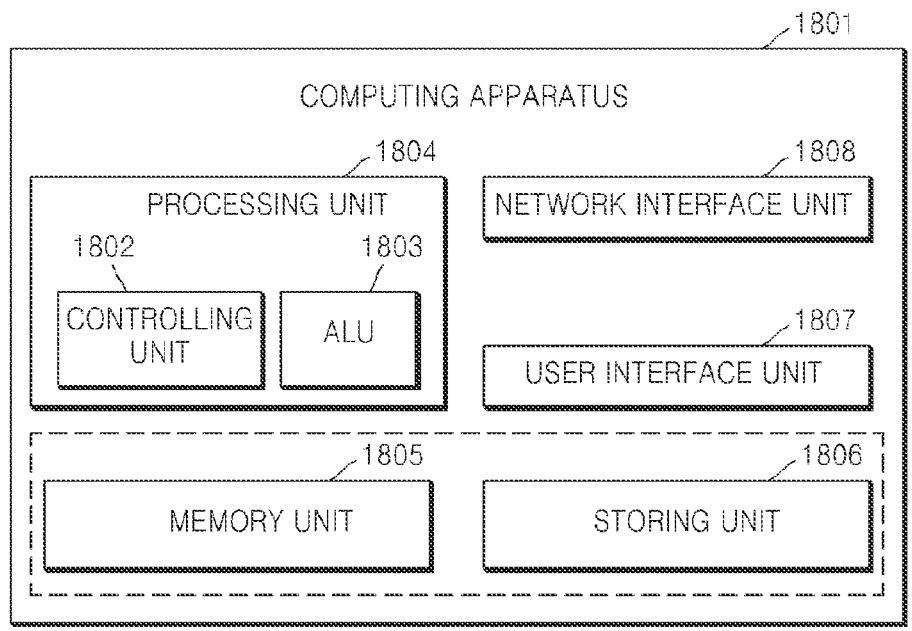
FIG. 18 illustrates a computing apparatus that performs the random access based compression and storage of NGS reads along with annotations, according to an embodiment of the present disclosure.

FIG. 18 illustrates a computing apparatus 1801 that performs the random access based compression and storage of nucleotide (e.g., based on NGS) reads along with annotations, according to an embodiment of the present disclosure.

Referring to FIG. 18, the computing apparatus 1801 includes a processing unit 1804 including a control unit 1802 and an Arithmetic Logic Unit (ALU) 1803, a memory 1805, a storage unit 1806, a network interface unit 1808, and a user interface unit 1807.

The processing unit 1804 functions to process instructions of an algorithm. The processing unit 1804 receives commands from the control unit 1802 so as to perform its processing. Also, any logical and arithmetic operations involving the execution of the instructions are computed with the help of the ALU 1803.

The computing apparatus 1801 may include multiple homogeneous and/or heterogeneous cores, multiple CPUs of different kinds, special media and other accelerators. The processing unit 1804 may be located on a single chip or over multiple chips.

The algorithm, including instructions and codes required for execution of the algorithm, is stored in either the memory unit 1805 or the storage unit 1806 or both. At the time of execution, the instructions may be fetched from the corresponding memory 1805 and/or the storage unit 1806 and may be executed by the processing unit 1804.

In one hardware implementation apparatus, the computing apparatus 1801 may be connected to various other devices via the network interface unit 1808, may receive a command from a user via the user interface unit 1807, or may provide the user with a processing result in the computing apparatus 1801.

Figure 19:
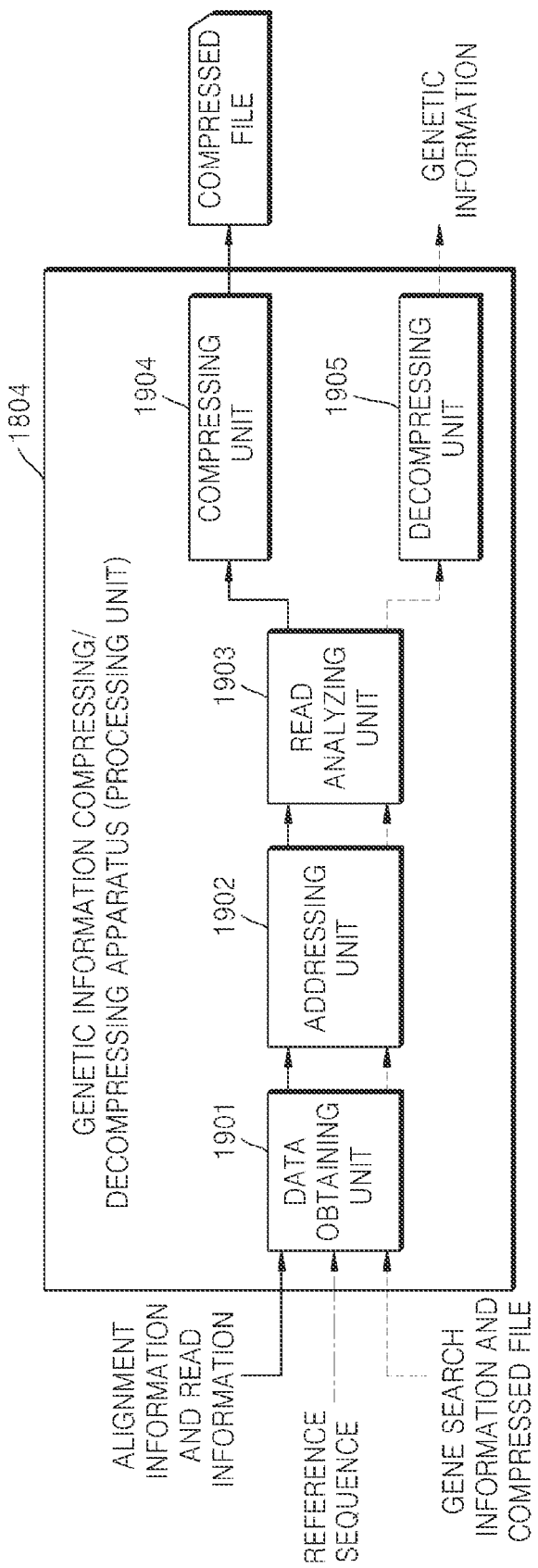
FIG. 19 is a diagram of a genetic information compressing/decompressing apparatus, according to an embodiment of the present disclosure.

FIG. 19 is a diagram of a genetic information compressing/decompressing apparatus, according to an embodiment of the present disclosure. Referring to FIG. 19, the genetic information compressing/decompressing apparatus corresponds to the processing unit 1804 of the computing apparatus 1801 described with reference to FIG. 18. Although descriptions are omitted, if the descriptions are described above with reference to FIGS. 1 through 17, the genetic information compressing/decompressing apparatus may perform operations and functions according to the descriptions of FIGS. 1 through 17.

The genetic information compressing/decompressing apparatus may be implemented as one or more processors. That is, the genetic information compressing/decompressing apparatus may be implemented as an array of a plurality of logic gates or may be implemented as combination of a general-use microprocessor and a memory storing a program that is executable by the microprocessor. Also, the genetic information compressing/decompressing apparatus may be implemented in the form of a module of an application program. Furthermore, it is obvious to one of ordinary skill in the art that the genetic information compressing/decompressing apparatus may be implemented as another hardware device capable of performing operations to be described in the present embodiment.

Although the genetic information compressing/decompressing apparatus shown in FIG. 19 only has elements related to the present embodiment so as to prevent the features of the invention from being obscured, the genetic information compressing/decompressing apparatus may further include other elements in addition to the elements shown in FIG. 19.

The genetic information compressing/decompressing apparatus compresses genetic information, e.g., obtained by using NGS. Also, the genetic information compressing/decompressing apparatus decompresses genetic information from a compression file responsive to, and by using, gene search information that is input from a user via the user interface unit 1807 (refer to FIG. 18) or the network interface unit 1808 (refer to FIG. 18).

First, operations and functions of elements of the genetic information compressing/decompressing apparatus are described below. In one embodiment, the genetic information compressing/decompressing apparatus includes a data obtaining unit 1901, an addressing unit 1902, a read analyzing unit 1903, a compressing unit 1904, and a decompressing unit 1905.

The data obtaining unit 1901 obtains read information about nucleotide reads, e.g., that are obtained using a NGS platform, and alignment information about positions of the reads that are aligned to a reference sequence. Also, the data obtaining unit 1901 obtains the reference sequence.

An addressing unit 1902 identifies an addressing scheme based on distribution of the reads aligned to the reference sequence. Here, when it is assumed that the reference sequence is divided into blocks having a constant length, the distribution of the aligned reads may be calculated by using a variation coefficient obtained from an average and standard deviation of the number of reads included in each of the assumed blocks. That is, the distribution of the aligned reads may be calculated by using Equation 3 that is described above.

When it is assumed that the reference sequence is divided into blocks having a constant length, the addressing unit 1902 may identify the addressing scheme based on a ratio of the number of empty blocks not including the reads to the total number of the assumed blocks. That is, the addressing scheme may be identified by using Equation 4c that is described above.

A read analyzing unit 1903 uses the addressing scheme that is identified by the addressing unit 1902. In more detail, the read analyzing unit 1903 uses one of an addressing scheme that corresponds to a case in which the reads are uniformly distributed in an entire length of the reference sequence, an addressing scheme that corresponds to a case in which the reads are not uniformly distributed in the reference sequence, and an addressing scheme that corresponds to a case in which the reads are uniformly distributed in only specific intervals on the reference sequence. Here, the addressing scheme used by the read analyzing unit 1903 may be but not limited to the CIR scheme or the CRB scheme.

Further, the read analyzing unit 1903 compares the reference sequence with the aligned reads and then obtains difference information about an error between bases of the reference sequence and bases of the aligned reads.

A compressing unit 1904 generates a compressed file including information about the used addressing scheme and addresses of the blocks that are grouped on the reference sequence. Also, the compressing unit 1904 may generate the compressed file further including the difference information and furthermore, the compressing unit 1904 may generate the compressed file further including annotations based on the difference information. Here, the annotations may be mapped to reads having genetic variations from among the aligned reads.

The compressed file generated by the compressing unit 1904 may include header information containing lengths of the aligned reads, a length of at least one block, and the used addressing scheme.

Next, operations and functions of elements of the genetic information compressing/decompressing apparatus, which involve decompressing genetic information from the compressed file based on the gene search information received from a user, are described below.

The genetic information compressing/decompressing apparatus may selectively search for the genetic information from the compressed file by using the gene search information that is input from a user via the user interface unit 1807 (refer to FIG. 18) or the network interface unit 1808 (refer to FIG. 18). Here, the input gene search information includes disease information, and block information or interval information with respect to the blocks of the reference sequence.

As described above, the compressed file is obtained by compressing information about the addressing scheme, address information, the difference information about the error between bases of the reference sequence and bases of the aligned reads, annotation information, and the like.

The data obtaining unit 1901 obtains the compressed file including encoded genetic information, the reference sequence, or the like.

The addressing unit 1902 obtains the address information of the blocks that are grouped on the reference sequence by using an addressing scheme, from the compressed file.

The read analyzing unit 1903 determines an address of a block corresponding to the input gene search information, by using the obtained address information.

A decompressing unit 1905 selectively decompresses the annotation information corresponding to the determined address, by using the obtained reference sequence and compressed file. That is, the decompressing unit 1905 selectively decompresses the read information corresponding to the annotation information, wherein the read information is about the reads that are aligned to the reference sequence.

Figure 20:
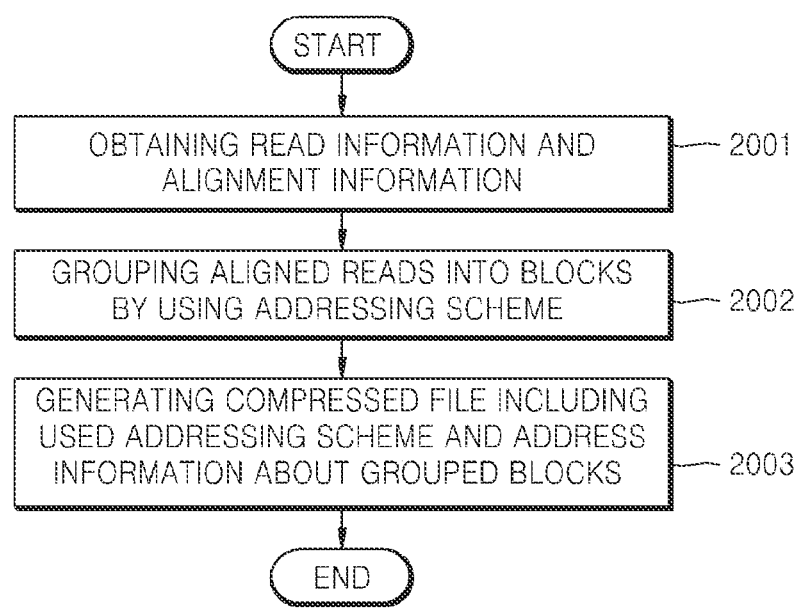
FIG. 20 is a flowchart of a method of compressing genetic information obtained by using NGS, according to an embodiment of the present disclosure.

FIG. 20 is a flowchart of a method of compressing genetic information, e.g., genetic information obtained using a NGS platform, according to an embodiment of the present disclosure. Referring to FIG. 20, the method involves operations that are performed in chronological order in the computing apparatus 1801 and the genetic information compressing/decompressing apparatus. Thus, hereinafter, although descriptions are omitted, if the descriptions are described above with reference to FIGS. 18 and 19, the descriptions may also be applied to the method of FIG. 20.

In operation 2001, the data obtaining unit 1901 obtains read information about reads, e.g., that are obtained using a NGS platform, and alignment information about positions of the reads that are aligned to a reference sequence.

In operation 2002, the read analyzing unit 1903 groups the aligned reads into one or more blocks corresponding to intervals, by using an addressing scheme for dividing the reference sequence into a plurality of intervals.

In operation 2003, the compressing unit 1904 generates a compressed file including the used addressing scheme, information about an address of the grouped blocks on the reference sequence, and the like.

Figure 21:
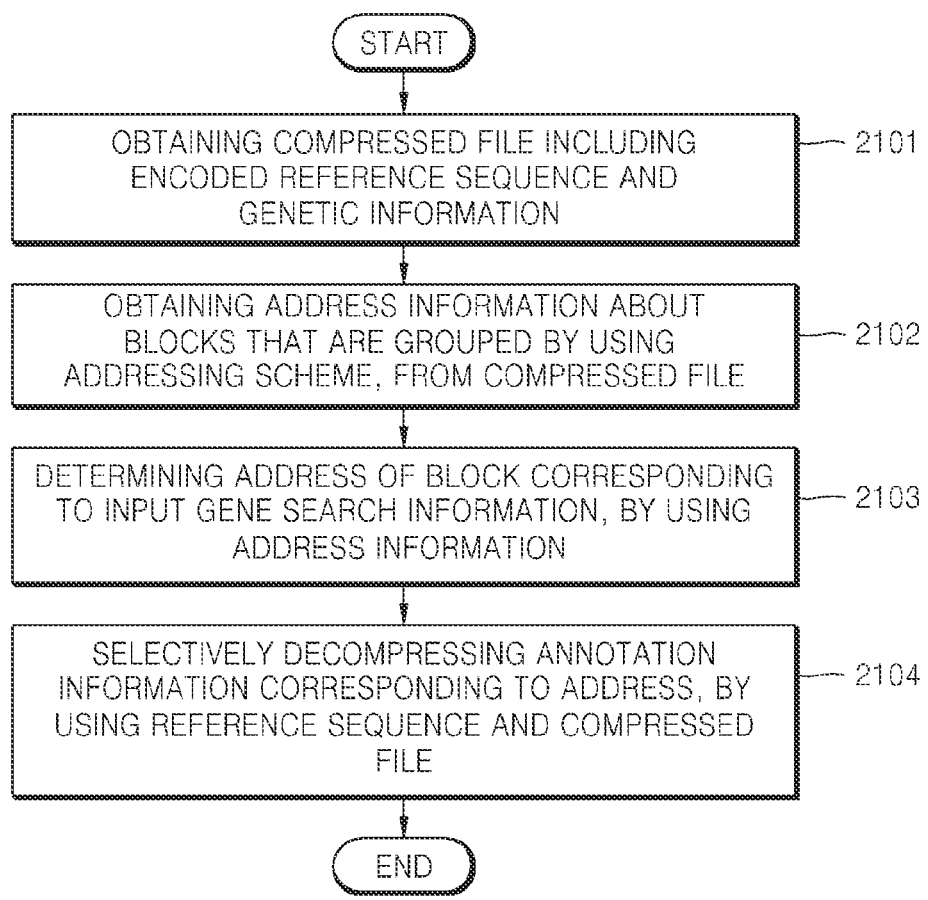
FIG. 21 is a flowchart of a method of decompressing genetic information by using gene search information that is input from a user, according to an embodiment of the present disclosure.

FIG. 21 is a flowchart of a method of decompressing genetic information by using gene search information that is input from a user, according to an embodiment of the present disclosure. Referring to FIG. 21, the method according to the present embodiment involves operations that are performed in chronological order in the computing apparatus 1801 and the genetic information compressing/decompressing apparatus 1900. Thus, hereinafter, although descriptions are omitted, if the descriptions are described above with reference to FIGS. 18 and 19, the descriptions may also be applied to the method of FIG. 21.

In operation 2101, the data obtaining unit 1901 obtains a compressed file including encoded genetic information, and a reference sequence.

In operation 2102, the addressing unit 1902 obtains address information of blocks that are grouped on the reference sequence by using an addressing scheme, from the compressed file.

In operation 2103, the read analyzing unit 1903 determines an address of a block corresponding to the input gene search information, by using the obtained address information.

In operation 2104, the decompressing unit 1905 selectively decompresses annotation information corresponding to the determined address, by using the obtained reference sequence and compressed file.

The embodiments of the present disclosure can be written as computer programs and can be implemented in general-use digital computers that execute the programs using a computer readable recording medium. In addition, a data structure used in the embodiments of the present disclosure can be written in a computer readable recording medium through various means. Examples of the computer readable recording medium include magnetic storage media (e.g., ROM, floppy disks, hard disks, etc.), optical recording media (e.g., CD-ROMs, or DVDs), etc.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of compressing genetic information, the method comprising:

obtaining read information about a plurality of nucleotide sequencing reads and alignment information about positions of the reads that are aligned to a reference sequence (aligned reads);

identifying an addressing scheme based on a distribution of the reads aligned to the reference sequence, the addressing scheme divides the reference sequence into intervals;

grouping the aligned reads into one or more blocks corresponding to the intervals based on the identified addressing scheme, wherein the grouping the aligned reads comprises grouping the aligned reads using the identified addressing scheme; and generating a compressed file comprising the addressing scheme and information about an address of the grouped blocks on the reference sequence, wherein the reference sequence is divided into blocks having a constant length, and the identifying the addressing scheme comprises identifying the addressing scheme based on a ratio of a number of empty blocks not comprising the reads to a total number of blocks.

2. The method of claim 1, wherein grouping the aligned reads comprises using one of an addressing scheme that corresponds to a case in which the reads are uniformly distributed in an entire length of the reference sequence, using an addressing scheme that corresponds to a case in which the reads are not uniformly distributed in the reference sequence, and using an addressing scheme that corresponds to a case in which the reads are uniformly distributed in a portion of the intervals on the reference sequence.

3. The method of claim 1, wherein the addressing scheme comprises at least one of a constant interval on reference (CIR) scheme in which the reference sequence is divided into a plurality of intervals having a constant length, and a constant number of reads per block (CRB) scheme in which the reference sequence is divided into a plurality of intervals where the one or more grouped blocks comprise a constant number of reads.

4. The method of claim 1, further comprising comparing the reference sequence with the aligned reads and then obtaining difference information about an error between bases of the reference sequence and bases of the aligned reads, and wherein the compressed file further comprises the obtained difference information.

5. The method of claim 4, wherein the difference information comprises information indicating occurrence of the error comprising at least one of insertion, substitution, and deletion with respect to the reference sequence.

6. The method of claim 4, further comprising obtaining annotations about genetic variations based on the obtained difference information, and wherein the compressed file further comprises the obtained annotations.

7. The method of claim 6, wherein the obtained annotations are mapped to reads having the genetic variations from among the aligned reads.

8. The method of claim 1, wherein the compressed file comprises header information including lengths of the aligned reads, a length of the one or more blocks, and the addressing scheme.

9. A method of compressing genetic information, the method comprising:
  obtaining read information about a plurality of nucleotide sequencing reads and alignment information about positions of the reads that are aligned to a reference sequence (aligned reads);
  identifying an addressing scheme based on a distribution of the reads aligned to the reference sequence, the addressing scheme divides the reference sequence into intervals;
  grouping the aligned reads into one or more blocks corresponding to the intervals based on the identified addressing scheme, wherein the grouping the aligned reads comprises grouping the aligned reads using the identified addressing scheme; and
  generating a compressed file comprising the addressing scheme and information about an address of the grouped blocks on the reference sequence wherein the reference sequence is divided into blocks having a constant length, and the distribution of the reads is calculated by using a variation coefficient obtained from an average and standard deviation of a number of reads comprised in each of the blocks.

10. A method of compressing genetic information, the method comprising:
  obtaining read information about a plurality of nucleotide sequencing reads and alignment information about positions of the reads that are aligned to a reference sequence (aligned reads);
  identifying an addressing scheme based on a distribution of the reads aligned to the reference sequence, the addressing scheme divides the reference sequence into intervals;
  grouping the aligned reads into one or more blocks corresponding to the intervals based on the identified addressing scheme; and
  generating a compressed file comprising the addressing scheme and information about an address of the grouped blocks on the reference sequence,
  wherein the addressing scheme comprises at least one of a constant interval on reference (CIR) scheme in which the reference sequence is divided into a plurality of intervals having a constant length, and a constant number of reads per block (CRB) scheme in which the reference sequence is divided into a plurality of intervals where the one or more grouped blocks comprise a constant number of reads, and wherein the CIR scheme comprises two variations in which a bit-mask to signify presence or absence of the reads in the one or more blocks is stored in each of the one or more blocks or is not stored.

11. The method of claim 10, wherein the bit-mask is not stored, and the compressed file comprises information about an address of the one or more blocks which includes the reads, and does not comprise information about an address of the one or more blocks which do not include the reads.

12. An apparatus for compressing genetic information, the apparatus comprising:
  a data obtaining unit configured to receive read information about a plurality of nucleotide sequencing reads, and alignment information about positions of the reads that are aligned to a reference sequence (aligned reads);
  an addressing unit configured to determine an addressing scheme based on distribution of the reads aligned to the reference sequence, the addressing scheme divides the reference sequence into intervals;
  a read analyzing unit configured to group the aligned reads into one or more blocks corresponding to the intervals based on the determined addressing scheme, wherein the read analyzing unit groups the aligned reads using the determined addressing scheme; and
  a compressing unit configured to generate a compressed file comprising the addressing scheme and information about an address of the grouped blocks on the reference sequence;
  wherein the data obtaining unit, the read analyzing unit, the read analyzing unit and the compressing unit are implemented by one or more processors, and wherein the reference sequence is divided into blocks having a constant length, and wherein the addressing unit determines the addressing scheme based on a ratio of a number of empty blocks not comprising the reads to a total number of blocks.

13. The apparatus of claim 12, wherein the addressing unit determines the addressing scheme based on distribution of the reads aligned to the reference sequence.

14. The apparatus of claim 12, wherein the read analyzing unit uses one of an addressing scheme that corresponds to a case in which the reads are uniformly distributed in an entire length of the reference sequence, an addressing scheme that corresponds to a case in which the reads are not uniformly distributed in the reference sequence, or an addressing scheme that corresponds to a case in which the reads are uniformly distributed in only specific intervals on the reference sequence.

15. The apparatus of claim 12, wherein the addressing scheme comprises at least one of a constant interval on reference (CIR) scheme in which the reference sequence is divided into a plurality of intervals having a constant length, or a constant number of reads per block (CRB) scheme in which the reference sequence is divided into a plurality of intervals whereby the one or more grouped blocks comprise a constant number of reads.

16. The apparatus of claim 12, wherein the read analyzing unit compares the reference sequence with the aligned reads and obtains difference information about an error between bases of the reference sequence and bases of the aligned reads, and wherein the compressing unit generates the compressed file by further adding the obtained difference information to the compressed file.

* * * * *

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Synthetic

<400> SEQUENCE: 1
ctggaccgga acatt                                                  15

<210> SEQ ID NO 2
<211> LENGTH: 15
<212> TYPE: DNA
<213> ORGANISM: Artificial Sequence
<220> FEATURE:
<223> OTHER INFORMATION: Synthetic

<400> SEQUENCE: 2
ctcgatcgga agatt                                                  15

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
ggaacatttc ttaggactgc tagctt                                      26

<210> SEQ ID NO 4
<211> LENGTH: 33
<212> TYPE: DNA
<213> ORGANISM: Artificial Sequence
<220> FEATURE:
<223> OTHER INFORMATION: Synthetic

<400> SEQUENCE: 4
ctcgatcgga agattcttag tgttagctag ctt                              33
```